(12) United States Patent
Lowe et al.

(10) Patent No.: US 9,907,626 B1
(45) Date of Patent: Mar. 6, 2018

(54) ORTHODONTIC ACCELERATOR

(71) Applicant: ORTHOACCEL TECHNOLOGIES INC., Bellaire, TX (US)

(72) Inventors: Michael K. Lowe, Bellaire, TX (US); Alex Bevly, Bellaire, TX (US); Ruru Chen, Bellaire, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 0 days.

(21) Appl. No.: 14/995,060

(22) Filed: Jan. 13, 2016

Related U.S. Application Data

(63) Continuation-in-part of application No. 13/973,865, filed on Aug. 22, 2013, now Pat. No. 8,939,762, which is a continuation of application No. 13/684,220, filed on Nov. 22, 2012, now Pat. No. 8,500,446, which is a continuation of application No. 13/609,346, filed on Sep. 11, 2012, which is a continuation-in-part of application No. 12/615,049, filed on Nov. 9, 2009, now Pat. No. 9,028,250, which is a continuation-in-part of application No. 11/773,849, filed on Jul. 5, 2007, said application No. 13/684,220 is a continuation-in-part of application No. 11/773,858, filed on Jul. 5, 2007, now abandoned.

(60) Provisional application No. 60/906,807, filed on Mar. 14, 2007.

(51) Int. Cl.
*A61C 7/08* (2006.01)
*A61C 7/12* (2006.01)
*A61C 7/00* (2006.01)

(52) U.S. Cl.
CPC .............. *A61C 7/008* (2013.01); *A61C 7/08* (2013.01); *A61C 7/12* (2013.01)

(58) Field of Classification Search
CPC .............. A61C 7/008; A61C 7/08; A61C 3/03
USPC .................................. 433/215, 2, 89, 18, 24
See application file for complete search history.

(56) References Cited

U.S. PATENT DOCUMENTS

| | | | |
|---|---|---|---|
| 5,496,256 A | 3/1996 | Bock | |
| 5,624,257 A * | 4/1997 | Farrell | A61C 7/08 128/861 |
| 6,158,439 A * | 12/2000 | Streetman | A61H 23/00 128/898 |
| 6,613,001 B1 | 8/2003 | Dworkin | |
| 6,648,639 B2 * | 11/2003 | Mao | A61C 7/22 433/18 |

(Continued)

FOREIGN PATENT DOCUMENTS

JP 2004321498 A * 11/2004

OTHER PUBLICATIONS

Werner, Alison. "Acceleration by Vibration." Orthodontic Products (2011): 31, 35.

(Continued)

*Primary Examiner* — Edward Moran
*Assistant Examiner* — Drew Folgmann
(74) *Attorney, Agent, or Firm* — Boulware & Valoir

(57) ABSTRACT

An improved vibrating orthodontic device is provided wherein motor speed is controlled by capacitive sensor, and thus lacks moving parts that are required by encoder use. The improved device also uses a tungsten offset weight, reducing size by more than 50%, yet still produces the needed force. The device is thus smaller, lighter and more robust.

17 Claims, 19 Drawing Sheets

(56) References Cited

U.S. PATENT DOCUMENTS

| | | | |
|---|---|---|---|
| 6,832,912 B2 * | 12/2004 | Mao | A61C 7/22 433/24 |
| 7,029,276 B2 | 4/2006 | Mao | |
| 7,409,741 B2 * | 8/2008 | Dworzan | A61C 17/3481 15/22.1 |
| 9,339,410 B2 * | 5/2016 | Smith | |
| 2004/0103905 A1 * | 6/2004 | Farrell | A63B 71/085 128/861 |
| 2006/0267427 A1 * | 11/2006 | Matsubara | H02K 7/063 310/81 |
| 2008/0233541 A1 | 9/2008 | De Vreese | |
| 2009/0090305 A1 * | 4/2009 | Cheok | A01K 15/02 119/707 |
| 2011/0088701 A1 * | 4/2011 | Thornton | A61F 5/566 128/848 |
| 2015/0003493 A1 * | 1/2015 | Bieck | B60R 21/015 374/51 |

OTHER PUBLICATIONS

Kau, C.H. "A novel device in orthodontics." Aesthetic Dentistry Today 3:6 (2009): 42-43.

Kau, C.H. "A radiographic analysis of tooth morphology following the use of a novel cyclical force device in orthodontics." Head & Face Medicine 7:14 (2011).

* cited by examiner

ORTHODONTIC ACCELERATOR

PRIOR RELATED APPLICATIONS

This application claims priority to U.S. Provisional Application Ser. No. 60/906,807, filed on Mar. 14, 2007, and is a Continuation-in-Part of U.S. application Ser. No. 11/773,849 (published as US20080227046) and U.S. application Ser. No. 11/773,858 (published as US20080227047), both filed Jul. 5, 2007, each of which is incorporated by reference herein in its entirety. This application is also a Continuation-in-Part of U.S. application Ser. No. 12/615,049 (U.S. Pat. No. 9,028,250), filed Nov. 9, 2009, US Application Ser. No. 13/609,346 (pending), filed on Sep. 11, 2012, Ser. No. 13/684,220 (U.S. Pat. No. 8,500,446), filed on Nov. 22, 2012, and Ser. No. 13/973,865 (pending), filed on Aug. 22, 2013. Each of these applications is incorporated by reference herein in its entirety for all purposes.

FIELD OF THE INVENTION

This invention relates to improved vibrating devices for use in accelerating orthodontic remodeling.

BACKGROUND OF THE INVENTION

A malocclusion is a misalignment of teeth or incorrect relation between the teeth of the two dental arches. The term was coined by Edward Angle, the "father of modern orthodontics," as a derivative of occlusion, which refers to the way opposing teeth meet. Angle based his classifications of malocclusions on the relative position of the maxillary first molar. According to Angle, the mesiobuccal cusp of the upper first molar should align with the buccal groove of the mandibular first molar. The teeth should all fit on a line of occlusion, which is a smooth curve through the central fossae and cingulum of the upper canines, and through the buccal cusp and incisal edges of the mandible. Any variation therefrom results in malocclusion.

There are three classes of malocclusions, Class I, II, and III. Further, class II is subdivided into three subtypes:

Class I: Neutrocclusion Here the molar relationship of the occlusion is normal or as described for the maxillary first molar, but the other teeth have problems like spacing, crowding, over or under eruption, etc.

Class II: Distocclusion (retrognathism, overjet) In this situation, the upper molars are placed not in the mesiobuccal groove, but anteriorly to it. Usually the mesiobuccal cusp rests in between the first mandibular molars and second premolars. There are two subtypes:

Class II Division 1: The molar relationships are like that of Class II and the anterior teeth are protruded.

Class II Division 2: The molar relationships are class II but the central incisors are retroclined and the lateral incisors are seen overlapping the central incisors.

Class III: Mesioclusion (prognathism, negative overjet) In this case the upper molars are placed not in the mesiobuccal groove, but posteriorly to it. The mesiobuccal cusp of the maxillary first molar lies posteriorly to the mesiobuccal groove of the mandibular first molar. This malocclusion is usually seen when the lower front teeth are more prominent than the upper front teeth. In such cases, the patient very often has either a large mandible or a short maxillary bone.

Orthodontics, formerly orthodontia (from Greek orthos "straight or proper or perfect"; and odous "tooth"), is the specialty concerned with the study and treatment of malocclusion (improper or dysfunctional bite), which may be a result of tooth irregularity, disproportionate facial skeleton relationship, or both. Orthodontics treats malocclusion through the displacement of teeth via bony remodeling and control and modification of facial growth.

Bone is remodeled by the concerted activities of 3 cell types—osteoblasts, osteocytes, and osteoclasts. Osteoblasts are the cells that produce bone extracellular matrix and are responsible for its mineralization. Osteoblasts also have endocrine activity through secretion of osteocalcin, which regulates fat and energy metabolism. These cells also control the differentiation and activity of osteoclasts. Osteocytes are osteoblasts that have been incorporated into bone matrix and are cells with extensive dendritic processes through which the cells communicate with other osteocytes and with osteoblasts. Mechanical loading is sensitized by the dendritic processes and transferred to biochemical responses involved in control of osteoblast and osteoclast function. Osteocytes also have endocrine activity by releasing fibroblast growth factor 23, which is involved in phosphate secretion in kidneys. Differentiation of osteoclast mononuclear progenitors to mature multinucleated osteoclasts is regulated by macrophage colony-stimulating factor and receptor activator of NF-κB ligand, expressed by stromal cells in bone marrow or osteoblasts in bone, as well as by osteocytes. The integrated endo- and paracrine control of osteoblasts, osteocytes, and osteoclasts is important for maintaining bone mass and for control of remodeling and modeling processes in bone, including during orthodontic-induced tooth movement.

The process of orthodontic bone remodeling has been traditionally accomplished by using a static mechanical force to induce bone remodeling, thereby enabling teeth to move. This widely accepted approach to treating malocclusion takes about twenty-four months on average to complete. In this approach, orthodontic braces, consisting of an archwire that applies a continuous static force and interfaces with brackets that are affixed to each tooth. Braces are used to treat a number of different classifications of clinical malocclusion, including underbites, overbites, cross bites, open bites, and crooked teeth, for both aesthetic and functional/structural reasons.

Orthodontic treatment is complicated by the fact that it is uncomfortable and/or painful for patients, and the orthodontic appliances are perceived as unaesthetic, all of which creates resistance to use. Further, the 24-month average treatment time is very long, and further reduces usage and compliance, which can include chronic poor dental hygiene. In fact, some estimates provide that less than half of the patients who could benefit from such treatment elect to pursue orthodontics.

Kesling introduced the tooth positioning appliance in 1945 as a method of refining the final stage of orthodontic finishing after debanding. A positioner was a one-piece pliable rubber appliance fabricated on the idealized wax set-ups for patients whose basic treatment was complete, but still needed a small amount of refinement. Kesling also predicted that certain major tooth movements could also be accomplished with a series of positioners fabricated from sequential tooth movements on the set-up as the treatment progressed. However, this idea did not become practical until the advent of 3D scanning and computer modeling in 1997.

Removable clear appliances, such as the Invisalign® system, have been introduced for treating malocclusion, and provide greatly improved aesthetics since the devices are transparent. However, because these appliances can be removed, compliance can be an issue, and failure to use slows overall treatment time.

As a treatment modality, aligners are also limited in the classifications of clinical malocclusion that they can address. In the past, aligners have not been able to easily rotate or extrude teeth because the aligner cannot adequately direct force in all directions. Being aware of these limitations, Align Technologies has recently combined the Invisalign® clear aligners with clear attachments that adhere to teeth and can provide a surface on which force can be exerted in any desired direction. A custom mold is made using a 3D model of the patients teeth with pockets therein for the placement of a force attachment, the placement and shape of which are determined using proprietary modeling software. The relevant force attachments are made and fitted into the mold, adhesive applied to the attachments, and the mold applied to the teeth. This allows precise and quick placement of the clear attachments, which are then affixed using light cure. There is some affect on aesthetics, but because the force attachments are also clear, they are not very noticeable from a distance.

In addition to static forces, cyclic forces can also be used for orthodontic remodeling. Kopher and Mao assessed cyclic forces of 5 N peak magnitude at 1 Hz in rabbits, while Peptan and Mao assessed cyclic forces of 1 N at 8 Hz in rabbits, and Vij and Mao assessed cyclic forces of 300 mN at 4 Hz in rats. In aggregate, the data from these three studies indicated that cyclic forces between 1 Hz and 8 Hz, with forces ranging from 0.3 N to 5 N, increased bone remodeling. Rates depended on different methodologies, but increases of 2.5× with vibrational forces were common.

The early Mao studies provided a basis for both possible efficacy and likely safety for using vibration in humans to assist orthodontic tooth movement. However, Mao's early experiments were performed on rabbit cranial suture closure model, and no device was ever built that could be used for human teeth. Thus, although suggestive, the work needed to be repeated on human teeth to prove its efficacy. However, no such device was available.

OrthoAccel® Technologies Inc., invented the first commercially successful dental vibrating device, as described in US20080027046, designed to apply cyclic forces to the dentition for accelerated remodeling purposes. Both intraoral and extraoral embodiments are described in US20080227046, each having processors to capture and transmit patient usage information. The bite plate was specially designed to contact occlusal as well as lingual and/or facial surfaces of the dentition, and thus was more effective than any prior art devices in conveying vibrational forces to the teeth.

Further, the device was tested in human clinical trials and shown to speed orthodontic remodeling as much as 50%. As such, it is truly a breakthrough in orthodontic technology (Kau 2010). Finally, the device is slim, capable of hands free operation, lacks the bulky head gear of the prior art devices, and has optimized force and frequency for orthodontic remodeling. Thus, its comfort level and compliance was also found to be high, with patients reporting that they liked the device, especially after the motor was redesigned to be quieter and smoother, as described in US20100055634 et seq. In fact, this device has been marketed as AcceleDent® in in several countries and has achieved remarkable commercial success since its recent introduction. AcceleDent® represents the first successful clinical approach to accelerate orthodontic tooth movement by modulating bone biology in a non-invasive and non-pharmacological manner.

However, further improvements in the above device are always beneficial, and this application addresses some of those improvements.

SUMMARY OF THE INVENTION

In one aspect, an orthodontic appliance includes an extraoral vibratory source and an intraoral dentition interface in the form of a bite plate or platform. A device interface couples the extraoral vibratory source to the intraoral attachment.

In another aspect, an orthodontic appliance includes an intraoral vibratory source and an intraoral bite plate or platform that comes into contact with the dentition.

Furthermore, the bite plate can contact the teeth at any point or at all points. The bite plate can contact occlusal surfaces, and preferably, the bite plate contacts lingual or facial (or both) surfaces of the teeth, although specialty plates can be designed for more complex clinical abnormalities.

A processor can control, sample, and compensate the extraoral or intraoral vibratory source. The processor runs software that captures usage frequency and duration and can be programmed to change the force, frequency, wave form, amplitude, duration or any other operating parameter. The processor can communicate usage frequency and duration to a remote computer via any type of wired or wireless communication method. The processor can communicate with the remote computer over the Internet, via smartphone, or simply with other devices (e.g. Bluetooth, Wireless LAN, etc.).

The processor can actively communicate with the user to provide input related to device use, especially related to biting too hard or not hard enough on the bite plate or platform. A mechanism can be provided to measure proper use based on moisture or temperature sensing, or salivary mineral content sensing, or other similar mechanisms, and feedback can be provided based on this control parameter as well. Pressure sensing technology would be needed to do this accurately, such as resistive strain gauges, capacitive or piezo elements.

Preferably, a custom or semi-custom application-specific integrated circuit (ASIC) is designed to drive the device, and is particularly preferred for a completely intraoral device. An ASIC can include entire microprocessors, memory blocks including ROM, RAM, EEPROM, Flash and other large building blocks. Such an ASIC is often termed a SoC (system-on-chip). Hardware description language (HDL), such as Verilog or VHDL, can be used to describe the functionality of ASICs. Field-programmable gate arrays (FPGA) are another option for driving the device. Programmable logic blocks and programmable interconnects allow the same FPGA to be used in many different applications. For smaller designs and/or lower production volumes, FPGAs may be more cost effective than an ASIC design even in production.

Another option is to use structured ASIC design (also referred to as "platform ASIC design"), because both manufacturing cycle time and design cycle time are reduced compared to cell-based ASIC, by virtue of there being pre-defined metal layers (thus reducing manufacturing time) and pre-characterization of what is on the silicon (thus reducing design cycle time). Design differentiation and customization is achieved by creating custom metal layers that create custom connections between predefined lower-layer logic elements. "Structured ASIC" technology is seen as bridging the gap between field-programmable gate arrays and "standard-cell" ASIC designs. Because only a small number of chip layers must be custom-produced, "structured ASIC" designs have much smaller non-recurring expenditures than "standard-cell" or "full-custom" chips, which require that a full mask set be produced for every design.

Important to usage compliance is that the device is comfortable and not unpleasant to use. The early models had variable speed and force, slowing when the patient exerted more force on the bite plate, and this irregular vibration caused some irritation and reduced compliance—A problem that could not be predicted from any prior art vibrational devices. Therefore, the device was redesigned for smoother (and quieter) operation.

In particular, a constant safe and effective vibration method was developed, said method comprising providing a vibrating motor with an encoder operably connected to a processor having software that counts a time between a first encoder event and a second encoder event; comparing said time to a target frequency; adjusting a motor speed via pulse width modulation to increase or decrease said motor speed as appropriate to maintain said target frequency; such that a vibrating orthodontic remodeling device comprising an intraoral bite plate and an extraoral vibration source employing said method vibrates at a single frequency between 20-40 Hz with a variance of ≤2 Hz (e.g., the frequency varies by only plus or minus 2 Hz from the desired frequency), and a single force between 0.1-0.5 N with a variance of +/−0.05 N (e.g, variation is ≤0.05 N) when said bite plate is bitten by a patient and said device is activated. With the re-designed software and mechanics allowing smoother vibration, compliance increased, allowing further improvement in the average speed of remodeling to be observed in the clinical trials.

Another method of maintaining a constant safe and effective orthodontic force and frequency, comprises providing a processor to control an offset weight vibration motor and a battery to power said processor and said motor; said processor interfacing with an acceleration sensor or an encoder on said motor; measuring a speed of said motor with said acceleration sensor or said encoder; and regulating said speed of said motor by pulse width modulation and by a dedicated voltage regulator that limits a drive voltage of said motor; such that an orthodontic remodeling device comprising an intraoral bite plate and an extraoral vibration source employing the method of steps a-d vibrates at a single frequency between 20-40 Hz with a variance of only 2 Hz, and a single force between 0.1-0.5 N with a variance of +/−0.05 N when said bite plate is bitten by a patient and said device is activated.

However, the above encoder design has moving parts that contributes to size and weight, and provides yet another point of failure for the device. Therefore, the design has been further updated herein. In the new design, motor speed control is achieved without any moving parts and with smaller components. Thus, size and weight can be further reduced.

The new motor control method uses pin headers placed somewhere on the circuit board or equivalent such that the header is 0.01-5 mm from the motor. These pin headers exhibit a small electrostatic (ES) field that is perturbed when the motor moves relative to the pins. A solid state sensor operably connected to the pin headers can measure this perturbation and can thus determine how fast the motor is rotating or otherwise moving. Software, similar to that described in other applications then adjusts motor speed to provide a constant speed, even under variable force.

Another option is to use an accelerometer, wherein a MEMS piezo-element forms a bridge, can detect movement. Such devices are commercially available, e.g., from STMicroelectronics or Freescale (now now NXP Semiconductor). Another option would be to use a gyroscope another way to do it, but this is a more costly option at this time.

A non-rechargeable or rechargeable battery can drive the vibratory source, wherein the rechargeable battery is charged using power from any type of power source including a USB port, RS-232 port, wall mount DC converter or a FireWire port, for example. Alternatively, the device can plug into any wall outlet.

Vibration is most commonly provided via a motor that rotates a shaft having an unbalanced or eccentric weight (off-set motor) or a piezoelectric based device, but any other vibrating means can be used. The known methods of producing vibration include motor and camshaft, motor and linkage, motor rack and pinion, motor and drive belt, and similar mechanical methods. However, solenoid vibrators, linear coil vibrators, linear resonance actuators, voice coil actuators, and the like can also be used. Existing commercial vibration motors include long life brushless (BLDC) vibration motors, coin (pancake) vibration motors, encapsulated vibration motors, pager motors, PCB mounted vibration motors, coreless DC motors, ultrasonic motors, to name but a few.

The ideal vibratory source would be quiet and combinable with a feedback mechanism to precisely control vibration speed and force. Further, it would be small, have a good working life at a cost effective price.

A large number of very small vibrating motors are available, as shown in the table below, but piezoelectric motors may be preferred due to the small size, and off-set weighted motors may be preferred due to low cost and availability. Particularly preferred are the substantially planar motors where the vibration is substantially parallel to the substrate (e.g., U.S. Pat. No. 5,554,971, U.S. Pat. No. 5,780,958, US20090224616, US20080129130, US20070103016, WO0178217, each incorporated by reference in its entirety).

| Company | Catalog | Size | Specifications |
| --- | --- | --- | --- |
| ELLIPTEC AG ™ | NA See U. S. Pat. No. 6,870,304 | 10 × 3 × 2 mm | 3-6 volts piezoelectric motor |
| SURPLUS TRADERS ™ | MF820 | 8 × 4 mm (0.315 × 0.1575 inches) | 1.5 to 4.5 VDC weighted shaft |
| SURPLUS TRADERS ™ | MF918 | 0.45 × 0.16 inches | 1 VDC to 5 VDC 18 ohms Weighted shaft |
| MOTOROLA ™ | G13566 | 0.44 × 0.18 inches | 1 VDC to 9 VDC 10 ohms Weighted shaft |

-continued

| Company | Catalog | Size | Specifications |
|---|---|---|---|
| SURPLUS TRADERS ™ | MF835 | 0.45 × 0.24 inches | 1.3 Vdc<br>100 mA<br>Weighted shaft |
| MATSUSHITA ™ | V0296A | 0.24 inch diameter | 1.5 VDC<br>Weighted shaft |
| SURPLUS TRADERS ™ | ME235 | 0.24 × 0.5 inches | 1.5 to 3 VDC<br>62 mA<br>weighted shaft |
| PRECISION MICRODRIVES ™ | 304-002 | 4 mm × 8 mm | 2.3 VDC to 3.6 VDC<br>100-120 mA<br>11000 rpm<br>Weighted shaft |
| PRECISION MICRODRIVES ™ | 308-100 | 3.4 × 8 | 2.-3.3 V, 120 mA<br>12000 rpm<br>8 mm Shaftless Vibration Motor |

Vibrations may be oscillating, random, directional, circular, and the like. Vibrators are described in the patent literature (and commercially available as seen above). For example, US20070299372, US20070255188, US20070208284, US20070179414, US20070161931, US20070161461, US20060287620, each incorporated by reference, describes various vibrating motors.

Batteries may drive the vibrational source, especially for intraoral embodiments. Small coin batteries, alkaline or lithium, are preferred due to their small size, but hydrogen batteries may also be preferred due to their shelf-life, power and power density, particularly as size and cost decrease with further technological development. A nickel metal hydride battery is currently preferred.

For certain embodiments, a battery that can be wirelessly recharged is preferred for longer product life (e.g., US20090051312, U.S. Pat. No. 7,511,454), but in other embodiments a low cost device is manufactured that is intended to be single patient use. It is known in the art to select an appropriate power source/motor combination to provide an orthodontic vibrator that vibrates within the frequency and power suitable for orthodontic remodeling.

Any off the shelf on/off switch can be used. Particularly preferred for the intraoral device is an on/off switch with depressible activator (push button, rocker or membrane button).

A leasing, rental or per procedure usage or any other variable usage systems as well as an outright purchase system enables the extraoral vibratory source or device to be provided to patients at low cost. The system can provide diagnostic information to a service provider. The system also supports recycling the extraoral vibratory source, although bite plates are intended to be single patient use components.

In a further aspect, the device delivers non-static forces to change dental tissue including a jaw, mandible or maxilla. The jaw receives sustained non-static forces (e.g., vibration) that are then delivered to the teeth constituents, and the non-static forces remodel the tissues of the mandible, maxilla, or jaw. The device can be used for other type of maxillofacial application and trauma like TMJ, Lefort trauma classification treatment procedures, tooth and other dental implants, among others.

In other aspects, inducing tooth movement and treating malocclusion, craniofacial anomalies, bony defects, and dentofacial deformities through accelerated bone remodeling are achieved by the delivery non-static forces; reducing pain and discomfort in patients; and improving tissue integrity long-term results as to prevent post-orthodontic treatment relapse.

The methods and apparatus include a mechanism for data capture and analysis related to patient compliance and usage behavior, as well as for establishing the invention as a component of the clinical office workflow to increase efficiency and productivity.

Advantages of the system may include one or more of the following. The system enhances and speeds the traditional orthodontic treatment process with the application of non-static forces. In accordance with one embodiment of the system, non-static forces are used to accelerate the remodeling of craniofacial bones in conjunction with orthodontic treatment. The system can be used to treat all forms and classifications of dental malocclusion, craniofacial anomaly, boney defect, or dentofacial deformity in which bone remodeling plays a physiological role. The system can be used exclusively in the maxilla, exclusively in the mandible, or in a dual-arch manner (both maxilla and mandible at the same time). Furthermore, the system can be used to treat cases presenting with a full dentition, any combination of naturally or unnaturally missing teeth, and to remodel bone in edentulous patients. Patients of any age and medical history profile can be treated. The system can be used by patients taking any type of medication.

The system enables orthodontic treatment and tooth movement to be considered in the broader context of bone remodeling. The rate-limiting step for orthodontic tooth movement is osteogenesis. Dynamic loading (cyclic forces) lead to greater osteogenesis or bone growth/bone remodeling, than static forces. Moving teeth is accomplished by remodeling the surrounding alveolar craniofacial bone. Bone remodeling involves several steps. First, net bone resorption occurs (osteoclastic activity) and takes two to three weeks. Second, reversal from net resorption to net formation (osteoblastic activity) takes place. Finally, bone formation fills the cavity in three to four months. Osteoclastic activity typically clears the path for tooth movement five to six times faster than osteoblastic activity fills it. Consequently, in order to speed up movement, bone formation (osteogenesis) must speed up.

Certain dynamic loading patterns (higher frequency and inserting rest periods, for example) greatly increase bone formation compared to basic dynamic loading, for example as 1 Hertz sinusoid. Inserting rest periods is known to be especially efficacious as it allows mechanosensitivity to be restored to the bone tissue. A point of diminishing returns is reached within each loading session. Therefore, intermittently loading and uploading with cyclic force can increase the rate of bone formation significantly.

The system enables an efficacious, yet quick treatment period that involves rapidly changing the forces on the teeth. This is done without requiring the introduction of piezoelectric currents to the mechanically stressed bone. Patient compliance is greatly enhanced through computer monitoring of usage. Treatment outcomes are directly dependent on how closely the patient follows the instructions of the healthcare professional. The system can be worn for a predetermined period such as approximately twenty minutes once a day or more, or any other suitable duration of time, thus the patient can wear the device at home for a modest wear duration.

The healthcare professional, patient, or parent/guardian can measure patient compliance and usage patterns that have occurred between appointments. The measured compliance and application is stored in electronic means, and is available for retrieval by the health care professional; including retrieval over the internet, by smartphone/smart device, or any other communication medium. Health care professionals may directly down load compliance information to readily available market practice software packages.

The system supports a business model that allows for a non-disposable component of the orthodontic treatment to be variable and proportional in cost to the duration of the treatment. The device can be disposable or non-disposable. The device can be leased, rented, or purchased on a procedure basis to the patient directly or through the orthodontist or by a third party. The proposed system also increases orthodontic case throughput and therefore office efficiency.

In more detail, the invention is an orthodontic remodeling device comprising an intraoral bite plate having a substantially U-shaped surface for contacting the occlusal surfaces of teeth, said U-shaped bite plate having an outside edge having upper and lower rims to contact an upper and lower facial surfaces of teeth and gums; said U-shaped bite plate has an inside edge having optional upper and lower rims to contact at least a portion of an upper and lower lingual surfaces of teeth and gums. There is also an extraoral waterproof housing containing a rechargeable battery operably coupled to a vibrator (actuator) operably coupled to a processor for capturing usage data operably coupled to a data-and-charging port for transmitting said data and charging said battery. The housing can also have an access hatch therein for accessing said data-and-charging port, but not said battery or processor. The U-shaped bite reversibly and operably connects to said housing, and the device is held in place during usage by teeth clamping on the bite plate, and lacks other head attachment means. This feature is particularly important for compliance, as head-gear is universally disliked by children and adults.

In another embodiment, the device is an orthodontic remodeling device comprising an intraoral bite plate having a substantially U-shaped surface for contacting an occlusal surface of teeth, said U-shaped bite plate having an outside edge having upper and lower rims to contact an upper and lower facial surfaces of teeth and gums; said U-shaped bite plate having an inside edge having upper and lower rims to contact at least a portion of an upper and lower lingual surfaces of teeth and gums; an extraoral waterproof housing containing a rechargeable battery operably coupled to a vibrator (or actuator) operably coupled to a processor operably coupled to a USB port; said housing also having an access hatch therein for accessing said USB port, but not the processor or battery, said access hatch tethered to said housing; said battery and/or access hatch accessible only with a tool; said U-shaped bite plate reversibly and operably connected to said housing; said orthodontic remodeling device having a noise level less than 55 dB when measured at 6 inches, and being capable of vibrating at a frequency of 20-40 Hz, with a variance of only 2 Hz, and a force of 0.1-0.5 Newtons, with a variance of +−0.05 N, or similar; wherein said device is held in place during usage by teeth clamping on the bite plate, and lacks other head attachment means.

In yet another embodiment, the device consists essentially of: an intraoral bite plate having a substantially U-shaped surface for contacting an occlusal surface of teeth, said U-shaped bite plate having an outside edge having upper and lower rims to contact an upper and lower facial surfaces of teeth and gums; said U-shaped bite plate having an inside edge having optional upper and lower rims to contact at least a portion of an upper and lower lingual surfaces of teeth and gums; an extraoral waterproof housing containing a charging port operably coupled to a rechargeable battery operably coupled to a vibrator (or actuator) operably coupled to a processor operably coupled to a data port; said U shape bite plate reversibly and operably connected to said housing; said orthodontic remodeling device having a noise level less than 55 dB when measured at 6 inches, and being capable of vibrating at a frequency of 20-40 Hz, with a variance of only 2 Hz, and a force of 0.1-0.5 Newtons, with a variance of +−0.05 N, or similar.

In another embodiment, the orthodontic device consists essentially of an extraoral vibratory source (or actuator); an extraoral processor that controls said extraoral vibratory source; a power source that drives said vibratory source; an intraoral attachment consisting of a bite plate allowing for contact with an occlusal surface and at least one of lingual and buccal surfaces of a patient's teeth, wherein a patient biting on said bite plate holds said device in place during use; wherein the extraoral vibratory source is coupled to the intraoral attachment; wherein said orthodontic device is hermetically sealed and can vibrate at a frequency of 0.1-400 Hz.

In another embodiment, the orthodontic device consisting essentially of an extraoral vibratory source (or actuator); an extraoral processor that controls said extraoral vibratory source and captures and transmits usage frequency and duration; a battery that drives said extraoral vibratory source; an intraoral attachment consisting of a bite plate allowing for contact with an occlusal surface and at least one of lingual and buccal surfaces of a patient's teeth, wherein a patient biting on said bite plate holds said device in place during use, wherein the intraoral attachment is coupled to the extraoral vibratory source; wherein said orthodontic device is hermetically sealed; wherein that when activated, said orthodontic device can vibrate at a frequency of 0.1-400 Hz.

In yet other embodiments, the device is completely intraoral, and the bite plate as described herein also has the power source, vibratory source, and processor directly thereon, although the processor can be omitted in a low cost device. The device should be hermetically sealed or otherwise waterproof, and thus wirelessly recharging batteries would be preferred, or long lasting batteries can be coupled with a low cost device. Since there is limited room inside the mouth a coin vibrator or other microvibrator may be the best vibratory source, coupled with e.g., a membrane button off/on switch, preferably accessible by the molars. Placement of these electronic components on the bite plate can either be buccal or lingual or occlusal, depending on the size of the components, but preferably is not labial (under the lips), as that interferes with use and aesthetics.

Methods of orthodontic remodeling, are also provided, comprising biting the bite plates, as described above, and activating the vibrator for about 5, 10, 15 or 20 minutes or more. This can be daily, or preferably twice daily, or more. Since the device speeds orthodontic remodeling, overall orthodontic treatment time is reduced, e.g., from an average of two years to one.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention. Thus, the term consisting essentially of excludes such elements as bulky head gear, designed to hold the device in place during use, tooth brush bristles, lasers, and the like, which would fundamentally change the nature and use of the device. The phrase would not, however, exclude elements such as additional LED lights, speed dials or other control buttons, battery charge indicators, accessories, variations in bite plate shape, variations in wiring, or variations in software, processor or communication technology, and the like.

As used herein, all nomenclature is per standard dental usage. Thus buccal surfaces, refers to cheek facing surfaces, labial to lip facing, lingual to tongue facing, and facial includes both labial and buccal facing surfaces.

By "U-shaped" what is meant herein is that the bite plates follow the curvature of the dentition, e.g., the biting surfaces of the teeth are in a substantially U-shaped curvature.

By "lingually shaped," what is meant is that a device is tongue shaped (e.g., like a U that has been filled in) such that it could function, e.g., as a palatal expander or retainer.

When we refer to contacting "the teeth" or similar phrase herein, what is meant is the entire dentition, e.g., the teeth of both arches. If less than the entire dentition is intended, it will be referred to as maxillary teeth, mandibular teeth, or a "portion" of the teeth or specific teeth or arches will be identified by name. Nevertheless, the bite plate need not contact every single tooth, since by definition some malocclusions may results in one or more teeth considerably out of alignment. The phrase also allows some leeway at the molars to accommodate the fact that dentition varies in size, and that molars erupt over 20-25 years of age, if at all, or may be removed to provide additional space for the remaining teeth, and thus most patients will not have a full set of adult teeth. Therefore, a bite plate intended to contact all teeth of the average youth patient, may not reach the molars of older or larger patients, or patients with more mature dentition.

By "treatment modality" what is meant is a mode of action that causes an orthodontic benefit.

By "treatment modality source," what is meant is a device or component of a device that provides the treatment modality. For example, vibration is an orthodontic treatment modality and a vibratory source provides vibration. A vibratory source could also be called a vibrator. Another treatment modality is infrared or ultraviolet light, and an LED or laser could be an exemplary light source.

A "bite plate" as used herein means a device worn inside the mouth and generally contacting occlusal surfaces of the teeth, such that the device is held by the patient "biting" on the bite plate.

An "extraoral driver" is the extraoral component that provides the treatment modality, and in preferred embodiments is a housing having an e.g., a treatment modality source such as a vibrator or laser, a processor, a battery or other power source, and the wiring needed to operatively couple or operate same, and wherein the housing has a socket for receiving the connector of the intra-oral bite plate. The housing will preferably be water resistant or waterproof.

By "socket" what is meant is a hole or recession or female end into which a male end connector can fit.

By "housing" is used for the exterior surface or container for the extraoral driver components.

"Orthodontic remodeling" is used consistently with its art-accepted definition, and refers to the realigning of teeth by boney remodeling under forces sufficient to provide osteoclastic activity on the high-pressure side, and osteoblastic activity on the reduced-pressure side, but with minimal root resorption, such that teeth are gradually moved and/or realigned to a desired position.

"Orthodontic forces" is used consistently with its art-accepted definition, and refers to the steady (static) realigning forces needed for orthodontic remodeling. Cf. Micropulses.

"Micropulses" are the very small vibrations or cyclic forces that are now known to cause 50% faster orthodontic remodeling when combined with an orthodontic force.

"Orthodontic remodeling appliances" or "orthodontic appliances" are used consistently with art-accepted definitions, and refers to those devices that provide orthodontic forces and thus the realigning of teeth. The term includes a variety of devices, such a braces, aligners, positioners, Herbst, sagittal appliance, palatal expander, pendulum, Nance, and the like. The term does not include tooth cleaning devices, such as electric toothbrushes, or professional cleaning tools such as scalers, and the like.

"Headgear" is used consistently with its art accepted definition, and refers to various head and neck attachment means used to provide orthodontic forces in a particular direction that cannot be easily be achieved with intra-oral attachment points. As one example, headgear might be used to pull the mandible forward to help correct class II malocclusions.

BRIEF DESCRIPTION OF THE DRAWINGS

FIG. 14A shows the overall graphic design, providing daily %, 30 day %, minutes of use and number of sessions on a single graph. The small horizontal bar with grey usage data on the bottom has movable cursors or scroll icons (see small boxes at each end) and allows the user to select the date range for viewing. Thus, the patient, parent/guardian, or healthcare professional can look at an entire multi-month or multi-year history, or can focus on the most recent month's usage. FIG. 14B shows how that data for a single day (see dots) can be selected for display by passing the cursor (arrow) over the data. The selected day's data is then displayed in the summary at the top right.

DETAILED DESCRIPTION OF THE INVENTION

In accordance with one embodiment of the invention, non-static forces (e.g., vibration) are used to accelerate the remodeling of craniofacial bones in conjunction with orthodontic treatment. The system can be used to treat all forms and classifications of dental malocclusion, craniofacial anomaly, boney defect, or dentofacial deformity in which bone remodeling plays a physiological role. The system can be used exclusively in the maxilla, exclusively in the mandible, or in a dual-arch manner (both maxilla and mandible at the same time). Furthermore, the system can be used to treat cases presenting with a full dentition, any combination of naturally or unnaturally missing teeth, and to remodel bone in edentulous patients. Patients of any age and medical history profile can be treated. The system can be used by patients taking any type of medication.

Figure 1A:
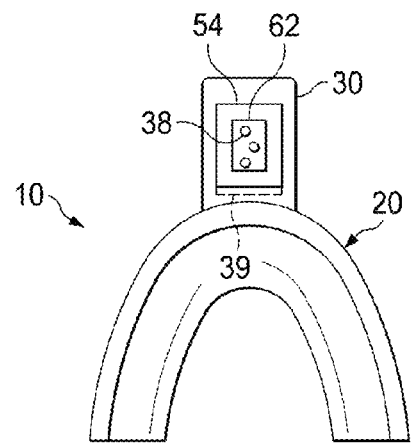
FIG. 1A-B shows one embodiment of an orthodontic treatment system, wherein the electrical components are all extraoral and contained within a housing.
Figure 1B:
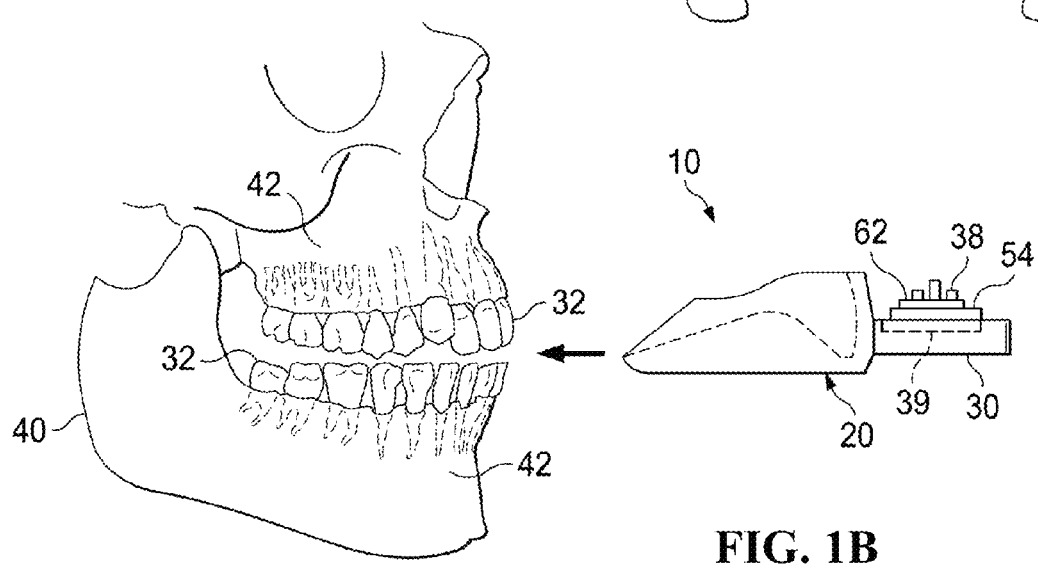

FIG. 1A-B shows one embodiment of an orthodontic device 10. The device 10 has an intraoral bite plate 20 that is inserted into a patient's mouth. The bite plate 20 is connected to an extraoral vibration source 30. The device 10 is held by the patient's jaw 40 clamping on the bite plate 20 to secure it between the dental arches 42. No other attachment means are needed, and thus this greatly simplifies the device and patient comfort, which serves to greatly improve compliance.

The bite plate 20 can interface with any part of the dentition 32, not being confined to a particular arch, region, quadrant, or tooth, and not being confined to either natural dentition or prosthetic dentition, although we have illustrated a generally useful shape herein, that contacts all teeth. By "all teeth" herein, we mean that the bite plate contacts from the most distal tooth through the most mesial tooth of both upper and lower arches. However, one or more teeth may not actually touch the bite plate due to malocclusion. If malocclusion is severe, the bite plate can be adapted through peel and stick risers to contact misaligned teeth or a custom bite plate can be built.

The extraoral vibration source 30 in this embodiment is activated by pushing a button 38 mounted on the extraoral apparatus. The vibrator could alternatively be activated by sensing the patient bite pressure as stimuli with a microprocessor 39 or some other mechanism translating the external stimuli into device function, including moisture or temperature sensing as well as salivary mineral content sensing.

The extraoral vibration source 30 in more detail includes a vibrator or actuator 54, which can be an off-set motor, piezoelectric vibrator, or any other means for producing vibration. The actuator 54 is operably coupled to the processor 39, which is operably coupled to battery 62. The extraoral vibration source 30 is also connected to the bite plate in such as way as to transfer the forces produced by actuator 54 to the bite plate 20 and thus the teeth and bone of the user. The entire extraoral vibration source 30 is preferably enclosed in a housing (not detailed in this figure), which is preferably watertight or at least water resistant. Furthermore, the wiring, software, connections, couplers and the like needed to make a functional vibratory source are not detailed in this figure, but various ways to implement same are known in the art.

Figure 2A:
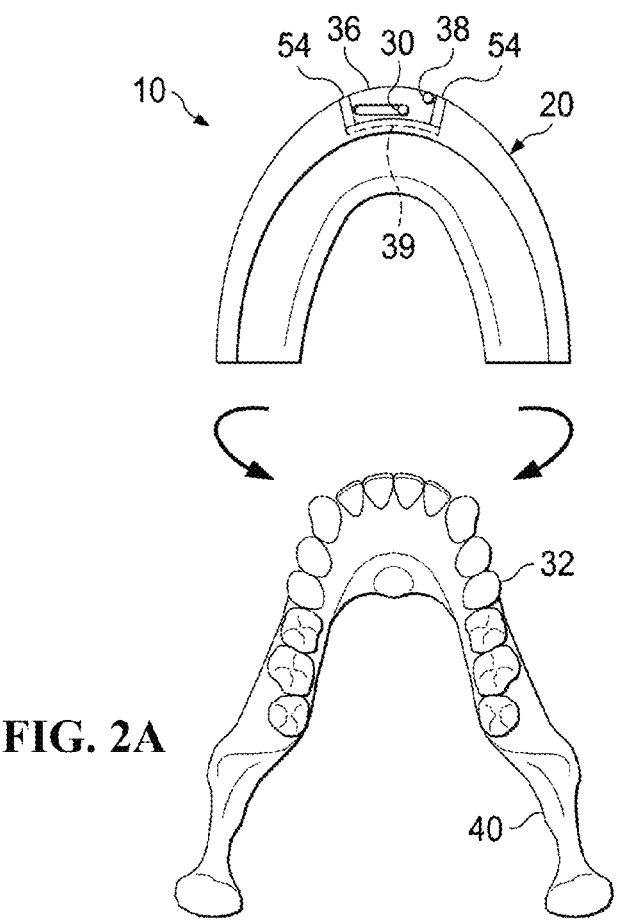
FIG. 2A-B shows a second embodiment of an orthodontic treatment system wherein all component are intraoral.
Figure 2B:
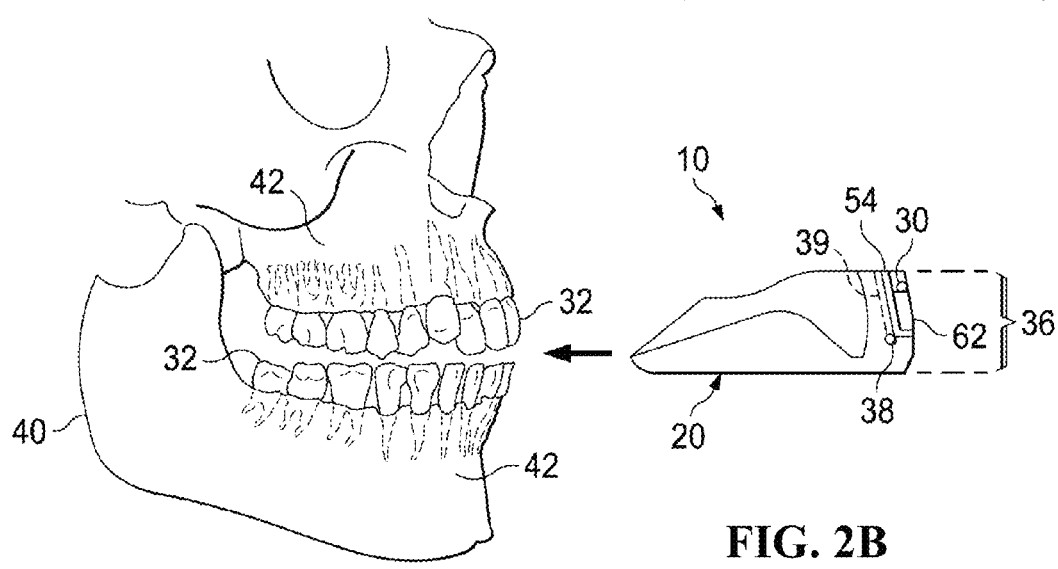

In another embodiment shown in FIG. 2A-B, the vibration source 30 is positioned intraorally and the bite plate holds the components necessary to generate and apply the force. This embodiment can generate and apply non-static forces to either the maxillary or mandibular arch or both. This particular embodiment involves a dual arch configuration that works with both dental arches 40. The patient inserts the bite plate 20 into the oral cavity and bites down, holding the device 10 steady between the teeth, regardless of which of the arches 40 the device is being activated for use. The vibration source 30 contained in the intraoral compartment 36 is activated by pushing a button 38, which activates actuator 54, causing the entire bite plate to vibrate. The vibration source 30 could alternatively be activated by sensing the patient bite pressure as stimuli with a microprocessor 39 or some other mechanism translating the external stimuli into device function.

An intraoral compartment on the midline and facial side of the device is shown, but it could also be contained on the lingual side, or two or more vibrators can be provided, e.g., on the molars. The entirety of the mechanism is hermetically sealed to render it waterproof.

In one embodiment, the device works when the patient applies sufficient force by biting on the device or otherwise clamping the jaws on the device. This enables the device to control the provision of cyclic forces when the correct amount of force is applied. In this embodiment, the device includes 1) microprocessor and compliance software and reporting system; 2) ability to provide cyclic forces at any level; and 3) the ability to only provide the cyclic force when the teeth apply the correct force on the device. An activation trigger can also be tied to some other stimuli including temperature or moisture sensing as well as salivary mineral content sensing.

Figure 3:
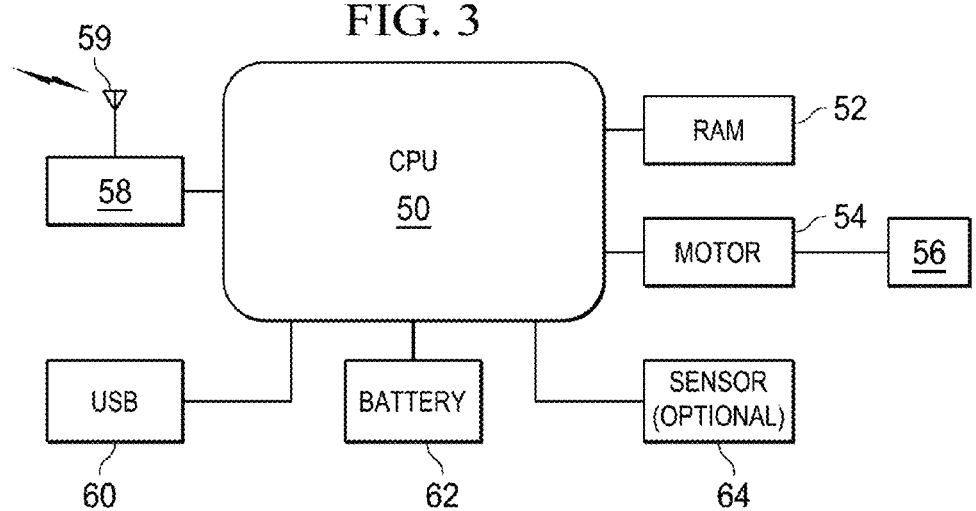
FIG. 3 shows an exemplary diagram of control electronics used with the system of FIGS. 1-2.

FIG. 3 shows a diagram of exemplary control electronics used with the device. The functional electromechanical components include a processor 39 that can be a low power microcontroller. The processor 39 stores instructions and data in its memory 52. The processor drives the actuator 54, such as an electrical motor or a piezoelectric device, among others. The system of FIG. 3 receives energy from a battery 62 that can be rechargeable. The processor 39 can be programmed or updated or transmit data through a communication port 60 such as a USB port or wireless transceiver 58 connected to an antenna 59. The battery 62 can be of any type and can be a rechargeable type with a docking port that recharges the battery upon insertion thereto. The processor 39 can also communicate with an optional sensor 64 to capture patient dental data if needed. The processor 39 can also simply transmit its operational parameters through the communication port 60 or the wireless transceiver 58 so that a dental professional such as a dentist, an orthodontist, a clinical trial monitor, a hygienist, a treatment coordinator, a staff member, a patient, or a third party can monitor treatment progress as required.

The actuator 54 can be directly attached to the bite plate or platform, as shown in the intraoral embodiment of FIG. 2, or be extraoral as shown in FIG. 1. Upon activation, the bite plate or platform, which can be of any shape or thickness, and comprised of any material, vibrates in a manner that delivers the necessary force. In preferred embodiments, the bite plate contains a solid inner core that is stiff enough to transmit vibration to the teeth, e.g., 30-40 Shore D, and is covered by a biocompatible coating or housing that is softer, e.g., 60-90 Shore A.

In yet other embodiments, the inner core is omitted, and instead the bite plate is made of a more firm durometer material, e.g., about 70-80 or 75 Shore A, such that the vibration at the housing and the vibration midway along the bite plate are nearly the same, suffering no more than a 0.05 N loss in traversing the stem and half the bite plate. In such an embodiment, the stem must be thick enough to allow a secure connection to the extraoral components, but as an alternative, the bite plate can be molded over the extraoral housing so that connectivity is not an issue. In such overmolded embodiments, it may be desirable to have an extraoral access compartment, such that the manufacture can access the electronics for repair. Preferably such compartment is not easily accessible by the user. Our testing of 3 different materials omitting the inner core/frame has not shown any degradation in force amplitude, so long as the vibrating element is firmly attached to the mouthpiece.

In order to measure the force, the bite plate is clamped on both sides to simulate a gentle bite, and the force sensor fed through a small hole in the clamp midway along the bite plate and force measured when the device is activated. Force is also measured at the socket of the extraoral driver on activation. In the current commercial embodiment, which has a stiff inner core made of polycarbonate, force at the socket is 0.28 N, and force midway along the bite plate is 0.25 N, and thus the loss is only 0.03 N (~10%). In our tests of a bite plate lacking an inner core, if we see at 15% loss, the motor weight will be modified accordingly to still deliver 0.2-0.25 N to the bite plate. However, these experiments are not yet complete.

To increase the force, there are 2 parameters that can be adjusted, mass and acceleration. Acceleration is controlled by the radius* of the weight. The mass is controlled by the material selection of the weight (e.g. tungsten, steel, etc.) and its dimensions.

An Eccentric Rotating Mass (ERM) is driven by a small DC motor. The Force (F) using an ERM is proportional to the radian speed of rotation (w), the Mass (m) of the rotating weight and Radius (r) of the center of gravity of the weight. The formula given is for the effective (root-mean-square) force applied.

$$F = \frac{mv^2}{r} = m\omega^2 r$$

The System shall sense the frequency of the force, and therefore vibration generated by the rotating ERM, with Capacitive Sensing of the metallic ERM.

Frequency=$2\pi\omega$

Frequency to Radian Speed Relationship

Figure 20:
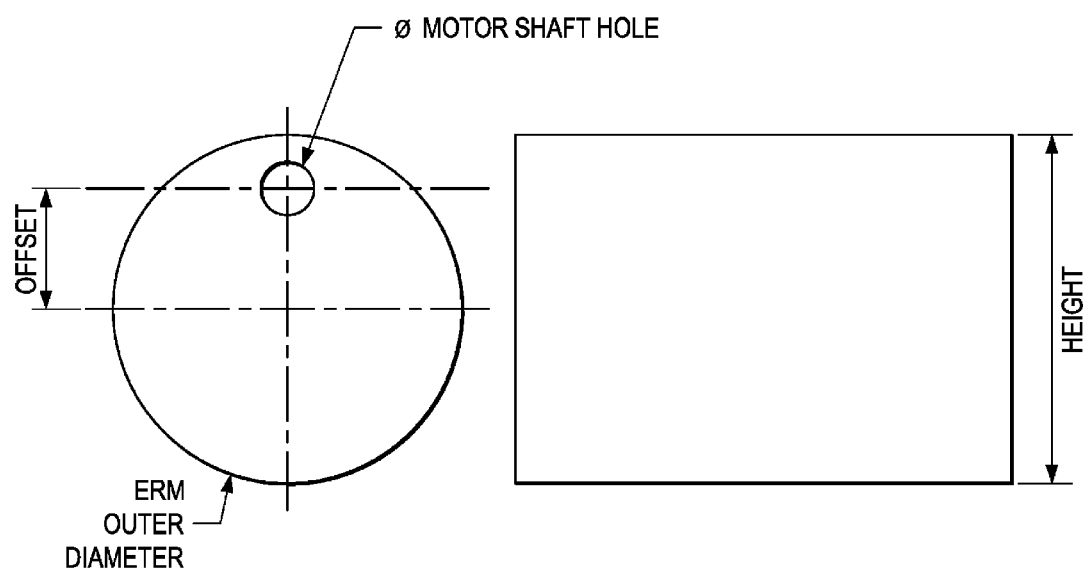
FIG. 20 shows the Frequency to Radian Speed Relationship.

*Radius=2×OFFSET, see FIG. 20.

One rationale for omitting the core, is that is reduced the parts and thus expense, but an important advantage is that possibly the bite plate can be thinner, which provides increased comfort, and also allows the user to trim the bite plate as needed for fit. Currently, the bite plate are provided in six different sizes, and it is anticipated that we can reduce that to 2 or 3 if the thickness of the bite plate is 2 mm or less such that it can be trimmed with scissors.

Besides the reduced part and process time expense already highlighted, additionally the bite plate and mouthpiece becomes more flexible when the rigid core is removed. This has allowed us to design a "Medium Flat" (dimensionally in between Large and Small Flat sizes) that could potentially accommodate all users given it can flex in (to Small) or out (to Large). This means a reduction to 1 size mouthpiece.

Figure 19:
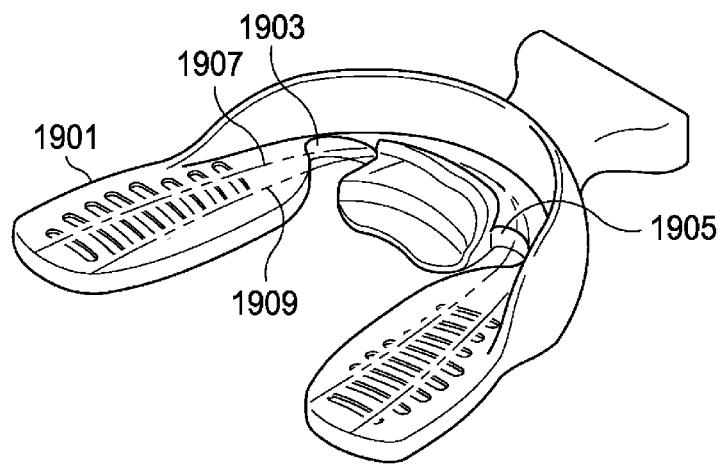
FIG. 19 shows a bite plate without inner core that has cutouts at about the canines such that the molar ends of the bite plate can move with respect to the front edge, thus accommodating Euro, Asian and Damon arch forms.

Furthermore, if a small wedge is cut out on the lingual side of the bite plate at about each incisor, the width of the bite plate can be adjusted to fit in the mouth, and thus accommodate each of the Euro, Asian and Damon arches, something that is not possible with the current design. FIG. 19 shows such wedges, and because the bite plate is e.g., made of a thermoplastic elastomer, such as medical grade silicone, it can bent at the wedges with minimal buckling to accommodate varying arches. On removal, the bite plate will return to its original configuration.

Preferably, the exterior of the bite plate will not have an objectionable taste and will be biocompatible, safe, and Food and Drug Administration-approved, such as silicone rubber, polypropylene, HDPE, and the like. In another embodiment the bite plate coating and other parts of the appliance that contact oral tissues have a selection of flavorings for additional comfort in use of the appliance. In yet another embodiment, the device is coated with a polymer that can be reshaped for custom fit, such as boil and bite polymers, or polymers that can be activated, cured and/or set with the addition of light and/or chemicals.

The device can have one or more interface points across the dentition, or can interface with the entire dentition in aggregate and in both arches simultaneously. The system embodied as the device described here pulsates or vibrates at a frequency of between about 0.1 Hertz to about 1200 Hertz, but 1-400 Hz is preferred, and especially 5-40 Hz or 30 Hz.

Ultrasonic frequencies might also be used, as there is some data showing the usefulness of ultrasound to speed bone remodeling. However, successful use in a dental application has not yet been shown. Further, it is possible that use of ultrasound may be very irritating in such proximity to the patient's head, thus rendering such a device of no value even if ultrasound is shown to have osteogenic effects. A device cannot have any efficacy if the patients won't use it.

In one embodiment, the interface with the dentition can transmit a force of about five Newtons (5N) for about twenty minutes a day at a frequency of between 0.1 to 400 Hz as discussed above. However, forces of less than 1 Newton, especially 0.1-0.5 or 0.2-0.3 N are more preferred by patients and have been shown to be clinically effective and without causing root resorption, which occurs if too much force is applied. Excess force is generally unpleasant to the patient, especially high force coupled with high frequency, and in preferred embodiments these parameters are adjustable within clinically acceptable limits. The commercial device has always used 0.25 N although this is sometimes rounded off to 0.2 N in the literature.

The prescribed clinical application of forces can be over any duration, frequency, and time of day combination pattern, but the current device is cleared for 20 minutes daily use. Upon completion of a twenty-minute duration of activation, the device can automatically shut off. Pacing indicators in the form of an audible tone, visual lights, cycle stutter, or by some other means provide feedback to the patient regarding elapsed time and time remaining in the current session of activation are also beneficial. These indicators can be of any form and frequency. A prototype system embodies the indicators as one second tones at five-minute intervals for the first fifteen minutes, representing a tone at minute five, minute ten, and minute fifteen; and then a final tone at minute nineteen, indicating that the user has 60 seconds of use remaining. Other indicators and/or suitable treatment intervals can be used to provide notice to the patient. For example, the professional can specify treatment intervals that mixes and matches the usage pattern to get to the 20 minutes such as 4×5 minutes or 10×2 minutes or some other combinations thereof.

After the device shuts off, the patient simply releases bite pressure from the intraoral bite plate and removes the device. Data capture related to usage frequency and duration updates in real time. As such, the device representation of this data post-use will indicate one additional session, and twenty additional minutes in duration of use, as compared to the same device immediately prior to the session.

In one embodiment, the battery 62 is rechargeable and can be inserted into its charger base between uses. Alternatively, the device can embed the battery 62 within its housing, and the entire device is placed into a rechargeable base (or the battery does not require re-charging). The charging of the battery can also be done using power received from the USB port 60, and this is particularly preferred. Thus, the charging port and the data port can be the same port. Alternatively, any suitable computer or electrical connection can be provided to charge the battery. For example, the battery can be charged using RS-232, Firewire, or through a 5V hook. Further, a standard wall mount DC converter can be used to charge the battery.

If a USB port is provided it should be protected inside the housing, and accessed via an access hatch or removable cap that is preferably tethered or somehow attached to the main body of the housing. While not essential for operability, it is preferred that the access hatch and battery be only accessible with a tool because this makes the device safer and eases the regulatory burdens. Alternatively, it may be possible to provide a waterproof USB port, but this will increase costs. Preferably, the battery and processor are not patient accessible either.

In one preferred device, the device uses inductive charging, having a base plate that contact the charging unit when the device is set thereon. Thus, no cables are needed, and it is easier to make a waterproof device this way.

The device is preferably hermetically sealed to be airtight and water tight, or at least water resistant, and can withstand exposure to water or moisture. It can and should be stored at room temperature. The battery 62 used in this particular embodiment is both memory-free and maintenance-free. The device can have a charger base, or can be inserted just long enough to charge for the next use.

The application of cyclic forces can be used to perform bone modeling and/or remodeling as well as more rapid tooth movement that may occur without bone modeling or remodeling. The bone remodeling and accelerated tooth movement across all types of displacement includes: rotation, translation, intrusion, extrusion, and tipping. This induced accelerated remodeling of bone is relevant for both the alignment and movement of teeth, in any plane, including horizontal and vertical, anterior and posterior, mesial and distal, and facial (e.g., buccal and labial) and lingual.

The delivery of the cyclic forces to the teeth and craniofacial bones can be facilitated by contact or any form of interaction with the dentition, including any tooth, group of teeth, or arch or by contact with braces or aligner or positioner. The interface can also include any dental tissue including tissues of the tooth, enamel, dentin, cementum, and pulp, and appliances, especially aligner trays, which can be of any commercial or non-commercial brand or design.

The device can be used to move either a single tooth, the entire dentition, or any combination of teeth groups. Teeth being displaced as a result of the non-static forces delivered by this device can include natural teeth without any dental work, natural teeth with dental work including operative restoration of any nature with any material, crown and bridge work, endodontically treated teeth, periodontally treated teeth, teeth surrounded by periodontally treated hard and soft tissue, and any type of dental implant, including micro implants used for orthodontic or tooth movement purposes. The proposed system can be used in conjunction with any type of dental or dentofacial surgery or treatment of trauma to any soft or hard tissue structure.

The system can be used in conjunction with lingual braces, facial braces, or any combination across either arch or any quadrant for both. It is also being contemplated as compatible with any robotics-based or other wire-bending optimization technology. The system is also compatible with clear aligner technology treatment plans, including the Invisalign® treatment approach, both with and without force attachments.

The system can be used in conjunction with a new treatment start from the very first appointment at which the orthodontic treatment begins, or it can be slotted into a treatment in progress at any point during the course of the treatment, up to and including the very last clinical stage.

In another aspect, the vibrating dental device can be used in conjunction with any currently used or in-development chemical, biochemical, and tissue engineering treatment approaches to accelerating tooth movement or remodeling craniofacial bone. These treatments may include growth factors, cytokines, matrix metalloproteinases (MMPs), tissue inhibitors of metalloproteinases (TIMPs), and regulation of extracellular matrix molecules. In addition, for both repositioning or stabilizing, tissue remodeling and/or an angiogenic substance(s) can be administered to the patient to promote remodeling of periodontal tissue surrounding the root(s) of the tooth or teeth to be moved. Preferred substance(s) will bind to and activate the relaxin receptor in the tissues which anchor the teeth or other craniofacial structures. Most preferred is relaxin or an analog or mimetic thereof which combines tissue remodeling activity with angiogenic activity. Analogs include peptides, oligomers, fragments, etc. which comprise the active region of native relaxin and mimetics include small molecule drugs, typically below 2 kD, designed to mimic the activity of native relaxin. Alternatively, substance(s) with predominantly angiogenic activity could be selected, such as VEGF, bFGF, estrogen, nitrous oxide, naltrexone, or the like. Further alternatively, collagenases or other tissue-softening enzymes could be utilized to promote periodontal tissue remodeling according to the present invention.

Figure 4:
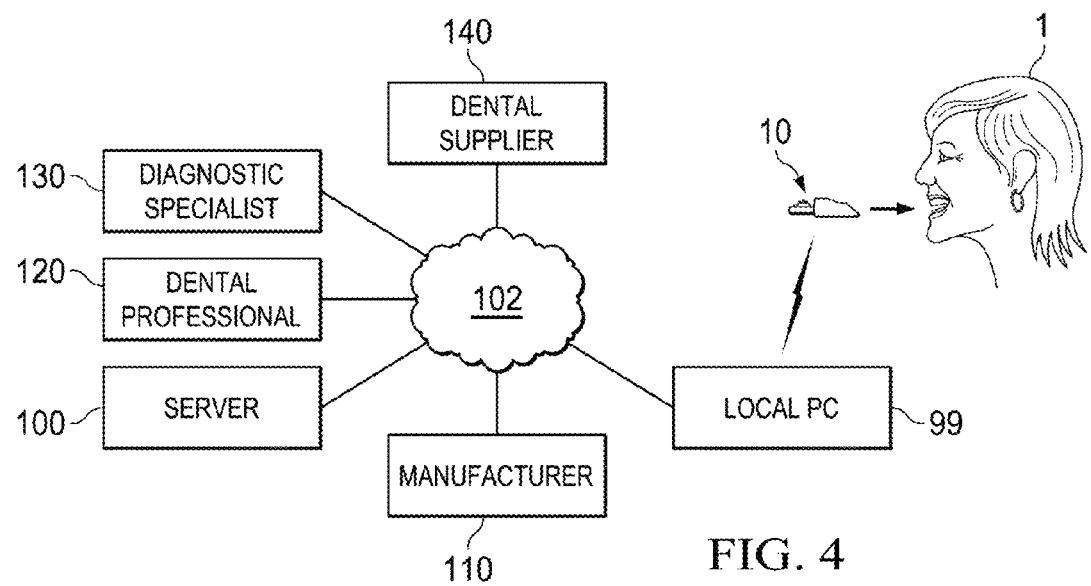
FIG. 4 shows an exemplary dental treatment network.

FIG. 4 shows an exemplary dental treatment network. The device 10 transmits operational and dental/medical information while embedded in a patient 1. The data is received by a local processor 99. The local processor 99 in turn uploads the information over a wide area network 102 such as the Internet. The data can be received by a treating professional such as a dentist or an orthodontist at workstation 120. The information can also be sent to one or more diagnostic specialists 130 who review the information and then make recommendation to the treating professional over the network 102. The information can also be sent to the device's manufacturer 110 and any other required dental supplier 140.

An Internet community with one or more dental supply companies, service providers, manufacturers, or marketers is connected to the network 102 and can communicate directly with users of the client workstations 99 or indirectly through the server 100. The Internet community provides the client workstations 99 with access to a network of orthodontic specialists and dental specialists. Additionally, the Internet community also provides access to a variety of supporting members such as financing firms, leasing firms and other service providers, among others.

In another embodiment, the device can send data to a smart phone, which can thus remind the user to use the device, or can send the data to third party for use in a clinical trial, or by dental practitioners or parents.

Although the server 100 can be an individual server, the server 100 can also be a cluster of redundant servers. Such a cluster can provide automatic data failover, protecting against both hardware and software faults. In this environment, a plurality of servers provides resources independent of each other until one of the servers fails. Each server can continuously monitor other servers. When one of the servers is unable to respond, the failover process begins. The surviving server acquires the shared drives and volumes of the failed server and mounts the volumes contained on the shared drives. Applications that use the shared drives can also be started on the surviving server after the failover. As soon as the failed server is booted up and the communication between servers indicates that the server is ready to own its shared drives, the servers automatically start the recovery process. Additionally, a server farm can be used. Network requests and server load conditions can be tracked in real time by the server farm controller, and the request can be distributed across the farm of servers to optimize responsiveness and system capacity. When necessary, the farm can automatically and transparently place additional server capacity in service as traffic load increases.

The server 100 can also be protected by a firewall. When the firewall receives a network packet from the network 102, it determines whether the transmission is authorized. If so, the firewall examines the header within the packet to determine what encryption algorithm was used to encrypt the packet. Using this algorithm and a secret key, the firewall decrypts the data and addresses of the source and destination firewalls and sends the data to the server 100. If both the source and destination are firewall protected, the only addresses visible (i.e., unencrypted) on the network are those of the firewall. The addresses of computers on the internal networks, and, hence, the internal network topology, are hidden. This is called "virtual private networking" (VPN).

Figure 5:
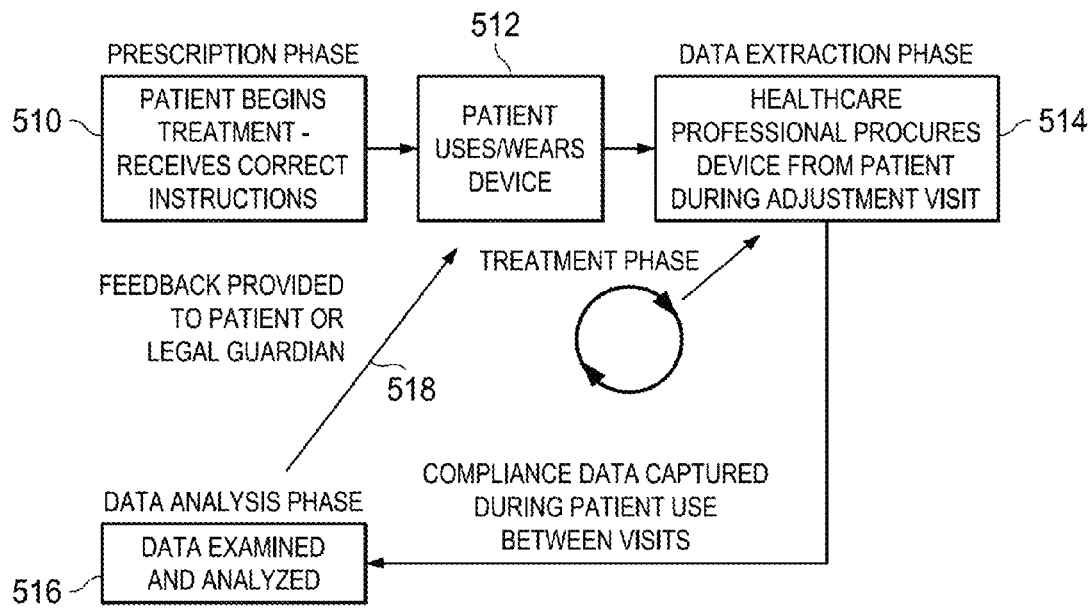
FIG. 5 shows an exemplary process for treating patients.

The system improves patient compliance, defined as duration of device use/wear, frequency of device use/wear, consistency in time of day device use/wear, and correct device use/wear such data is captured in data form by the device. Compliance refers to both not overusing and not underusing the device in accordance with the instructions given to the patient by the healthcare professional. This data can be viewed by the healthcare professional, as shown in FIG. 5. In this embodiment, instructions for use and wear are provided to the patient by the healthcare professional 510. The patient uses/wears the device, and data on compliance is captured during patient use 512. After each treatment period, the device is retrieved by the professional and compliance data is extracted therefrom 514. The data is presented in a form that will allow for data analysis by the healthcare professional 516. As a part of an active feedback process 518, the healthcare professional then makes recommendations, or re-prescribes, the device for subsequent use until the next visit or interaction. This process can involve some form of reward or punishment based on the compliance and usage pattern results. Alternatively, the device can be configured to automatically communicate usage to a central location, e.g., via smartphone and thus near real-time monitoring will be possible.

Figure 6:
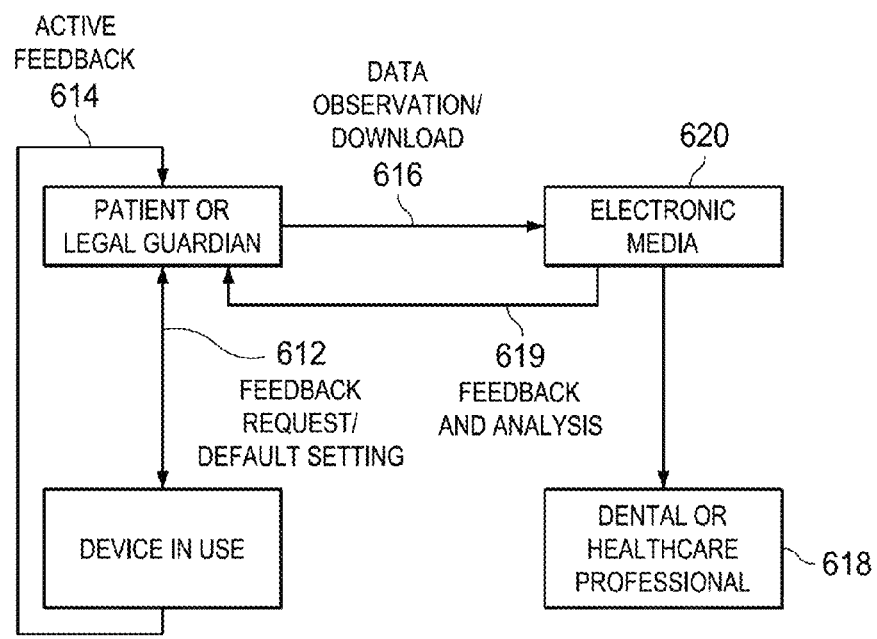
FIG. 6 shows an exemplary process to capture data and provide data for feedback purposes.

As shown in FIG. 6, the data can be provided either directly to the patient or to the legal guardian for feedback purposes as well. The device can be configured as seen in FIG. 6 to provide either active or passive feedback to the patient user. This data generation and observation can be enabled by a request via download with some form of electronic media, or delivered as a default setting during use. For example, during use, the device can provide visual feedback upon request 612 from the patient or automatically 614. The data can be downloaded 616 into an electronic media 620 such as a flash drive and the information can be sent to the professional for feedback and analysis 618, or to the patient directly or to the legal guardian of the patient 619.

Figure 7:
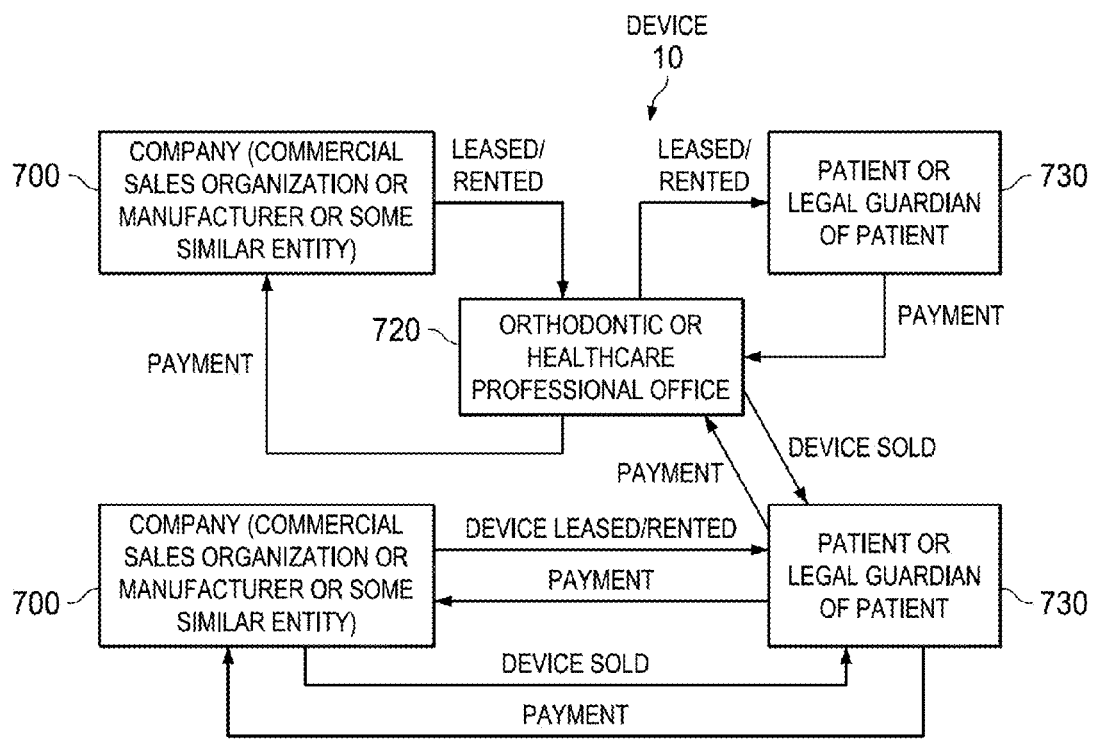
FIG. 7 shows an exemplary system for leasing, renting or purchasing the appliances.

FIG. 7 demonstrates an exemplary distribution system by company 700 where the device 10 is leased or rented to the patient 730 through the orthodontic office 720, allowing for the patient fee to be proportional to the amount of time that the device is used as a part of the treatment. Alternatively, the patient could rent or lease the device directly from the commercial sales organization or manufacturer as demonstrated in FIG. 7. The patient could also purchase the appliance instead of leasing or renting the device 10, either from the orthodontic or healthcare professional office 720 or from the commercial sales organization or manufacturer 700.

An additional aspect of the proposed system is related to the efficiency improvement that it allows and enables within the orthodontic or other healthcare professional office. It can be used to decrease treatment duration times, increase the number of new starts, improve financial performance of the practice across any metric, attract new patients, recruit former treatment-rejecters, and improve relations with upstream or downstream referring or referral dental/medical professionals of any discipline or specialty.

Figure 8:
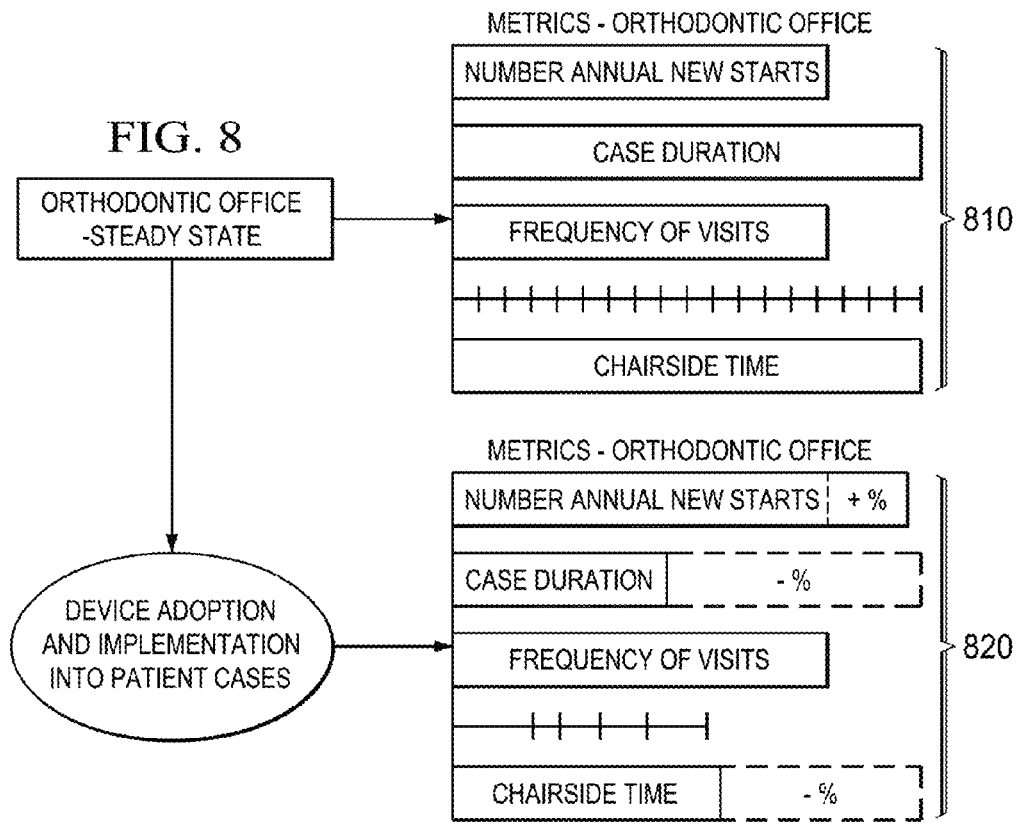
FIG. 8 shows an exemplary process for improving office and case efficiency.

Healthcare professional efficiency increases as a result of patients using the system. This improvement could include metrics such as an increased number of new case starts, a shorter duration of total treatment time, frequency of recall or adjustment visits, or a decreased amount of chair time, as shown in FIG. 8. In FIG. 8, the orthodontic office exists in a steady state in office and case efficiency without the device 810. As the adoption of the technology is increased and the devices are incorporated into patient cases, an improvement in the office and case efficiency is achieved 820. These efficiency improvements can occur as a part of or as a result of any stage of orthodontic treatment of any malocclusion classification, and with any archwire or appliance type, including all wire sizes, shapes, and compositions.

Figure 9:
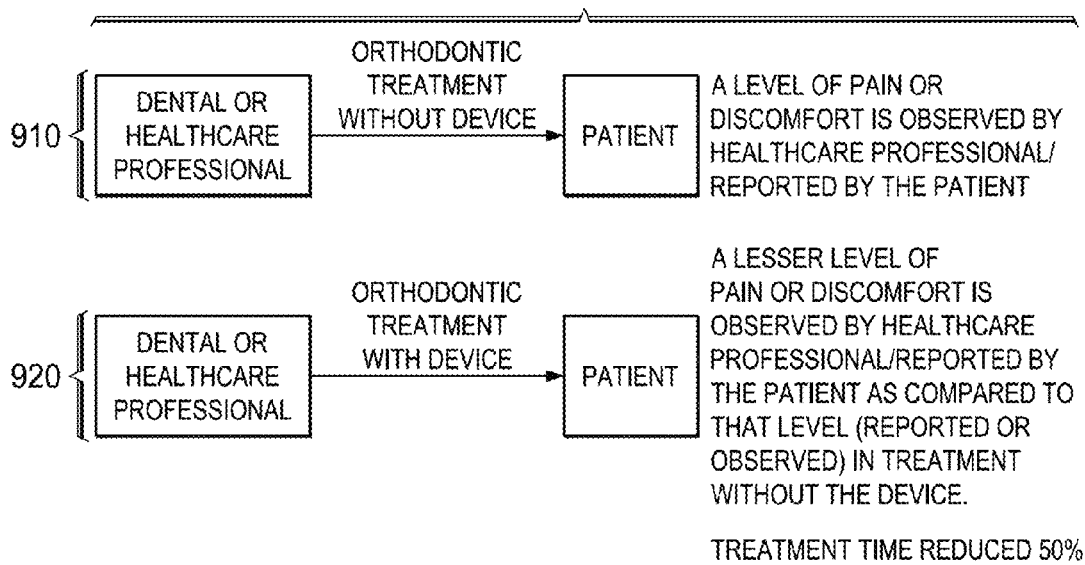
FIG. 9 is an exemplary process to compare differences in pain level and improved treatment time for patients treated with and without the appliances.

FIG. 9 shows an exemplary process to compare differences in pain level and integrity of clinical outcomes, respectively, for patients treated with and without the devices invented herein. FIG. 9 demonstrates a decrease in patient pain and discomfort as a result of using the device, and also that treatment time is substantially reduced (by as much as 50%, depending on compliance). In FIG. 9 the healthcare professional treats the patient without the device of the present invention 910 and the level of pain and/or discomfort is observed by the treating professional or reported by the patient. The healthcare professional then treats the patient with the device of the present invention and the level of pain and/or discomfort is observed by the treating professional or reported by the patient is captured 920. The difference between the pain level in patients treated with or without the device can be analyzed. The device treats patient with less pain, and the treatment result could be in the form of improved tissue integrity. Similarly, improved treatment times, by as much as 50% are shown, and this level of benefit has been clinically validated.

Figure 10A:
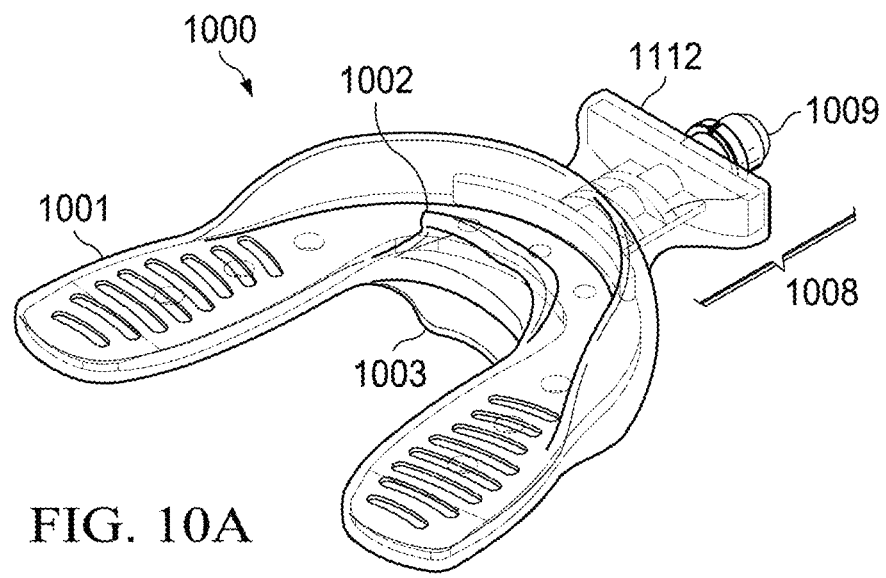
FIG. 10A-B shows a perspective view of a bite plate from two angles, showing the flat U-shaped base, and upper and lower lingual and facials rims, as well as the stem, which fits into a mating socket on the extraoral housing (not shown).
Figure 10B:
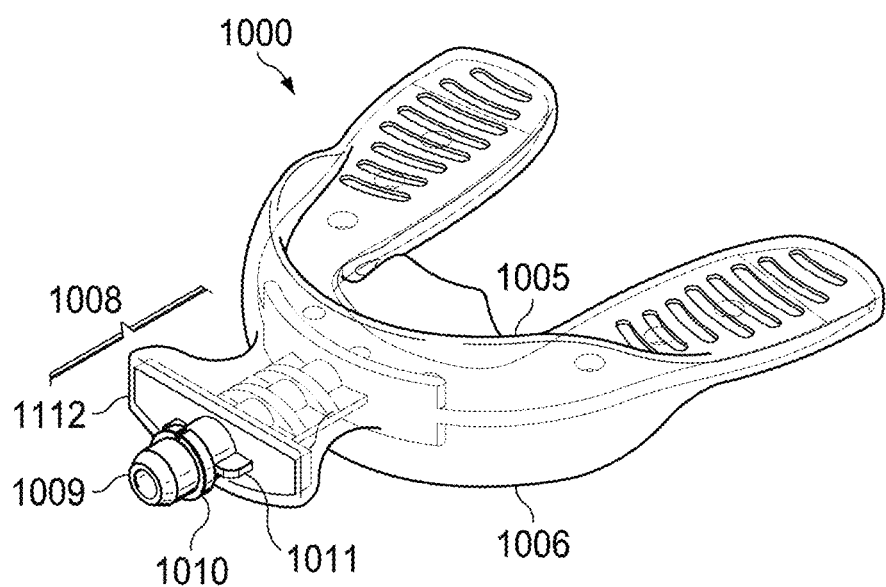

FIG. 10A-B shows an improved bite plate 1000, having generally U-shaped base 1001 that contacts occlusal surfaces of the teeth, the base having front and back edges, one or both edges having a rim to contact the facial and lingual surfaces of teeth and/or gums. Thus, upper lingual rim 1002, lower lingual rim 1003, upper facial rim 1005 and lower facial rim 1006 are shown. In this instance, the lingual rims contact only the incisors and/or canines, but not the molars. However, the rims can be varied in length to contact all, or a portion, of the teeth. It is preferred that at least one rim contact each tooth, except for specially designed bite plates made to correct extreme abnormalities.

Also shown in FIG. 10A-B is the stem 1008, which is the portion of the bite plate 1000 that mates with a corresponding socket in the extraoral housing (not shown here). In more detail, a cylindrical shaft 1009 is shown, having a groove (see FIG. 11) into which a jump ring 1010 fits, and mates with a corresponding depression in the socket. Optional flare 1112 is also shown, and is configured to provide an appropriate surface so that the user can push the stem into the socket. Because of this snap-fit feature between the bite plate and the extraoral housing, the bite plate can therefore reversibly connect to the extraoral housing, which enables easier cleaning and/or storage.

The thickness of the biocompatible overlay material can be adjusted to compensate for various patient bite configurations (open, deep, flat), as detailed in US20100055634, incorporated by reference herein. However, in most instances a bite plate that is slightly thinner at the distal end than the mesial end will accommodate the hinged nature of the temperomandibular joint and facial skeleton.

Thus, if a U-shaped bite plate has two back ends that can contact one or more distal or posterior teeth, and a front end that can contact one or more mesial or anterior teeth, and a thickness E, wherein said thickness E is 2-10 mm, the bite plate can be in one of three configurations:
a) thickness E does not substantially vary from said front end to said back ends;
b) thickness E increases from E at said front end to E plus 0.5-10 mm at said back ends;
c) thickness E increases from E at said back end to E plus 0.5-10 mm towards said front end.

We have shown the stem on the bite plate, but the bite plate may contain the socket, and the extraoral component may have the stem. Further, we have shown a cylindrical shaft with jump ring circumnavigating the shaft (a cylindrical type snap fit), as one example of a reversible coupling mechanism, but any reversible coupling mechanism could be employed, including a cantilevered beam snap fit, a spherical snap-fit, depressible push pins and sockets, a threadable screw fit, and the like.

Figure 11A:
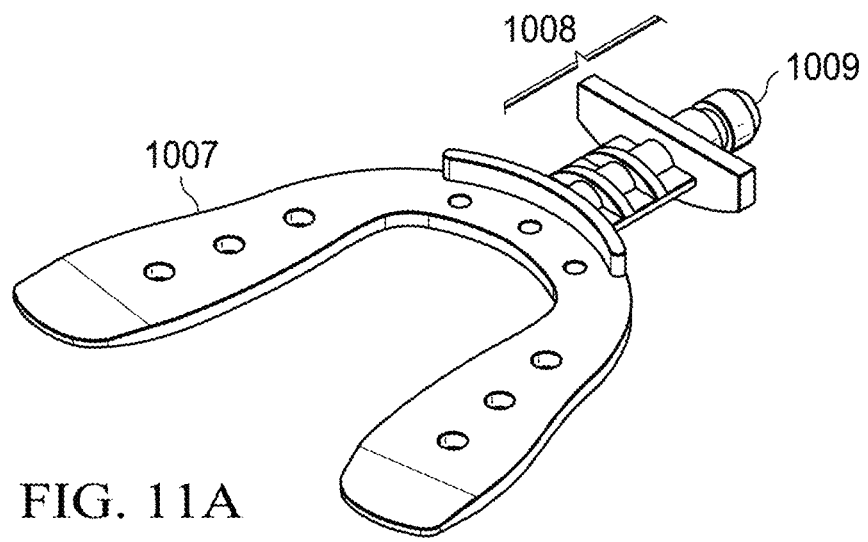
FIGS. 11 A and B shows the core of the bite plate from two angles, over which is molded a biocompatible overlay having the rims and desired final shape.
Figure 11B:
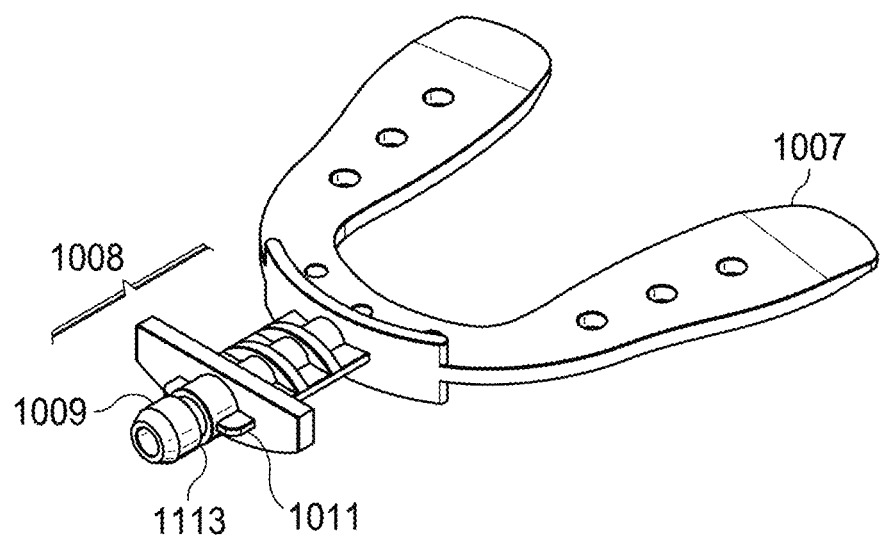

FIG. 11 shows the core 1007 of the bite plate, typically made from a resin, metal or ceramic having a harder durometer than the outer surface, and providing sufficient rigidity to the stem 1008 so as to allow it to lockingly fit into the socket. Cylindrical shaft 1009 has a groove 1113, into which jump ring 1010 fits. Also featured are locking pins 1011 and orientation pins (not shown), which prevent the bite plate from being inserted upside down. Generally plastics of at least 40 Shore D are used for the core, but metals or ceramics could also be used. A coating is provided over this core, and provides the final shape of the bite plate, as shown in FIG. 10. Such coating should be a biocompatible soft polymer of 40-70 Shore A, and particularly preferred is a medical grade, clear silicone.

Figure 12:
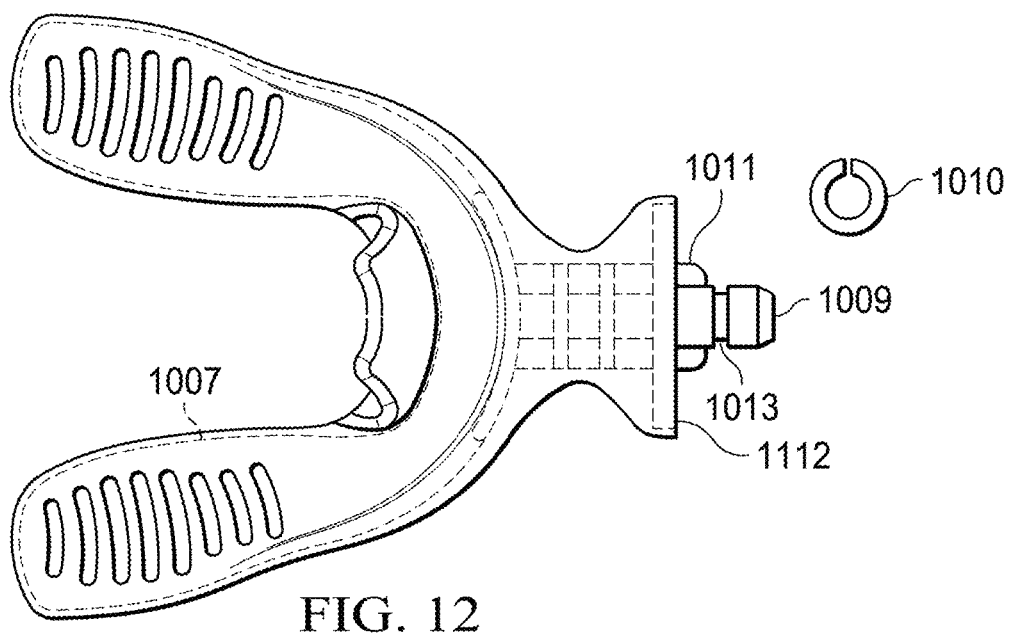
FIG. 12 shows a top view of the bite plate, more clearly illustrating the stem, flare, pins, cylindrical shaft and groove, into which fits the jump ring that mates with a corresponding recess in the socket (not shown).

FIG. 12 shows a top plan view of the bite plate, more clearly illustrating the core 1007, shaft 1009, flare 1112, pins 1011 and jump ring 1010, as well as the other edge of the overcoat, which provides the actual shape of the bite plate.

Figure 13A:
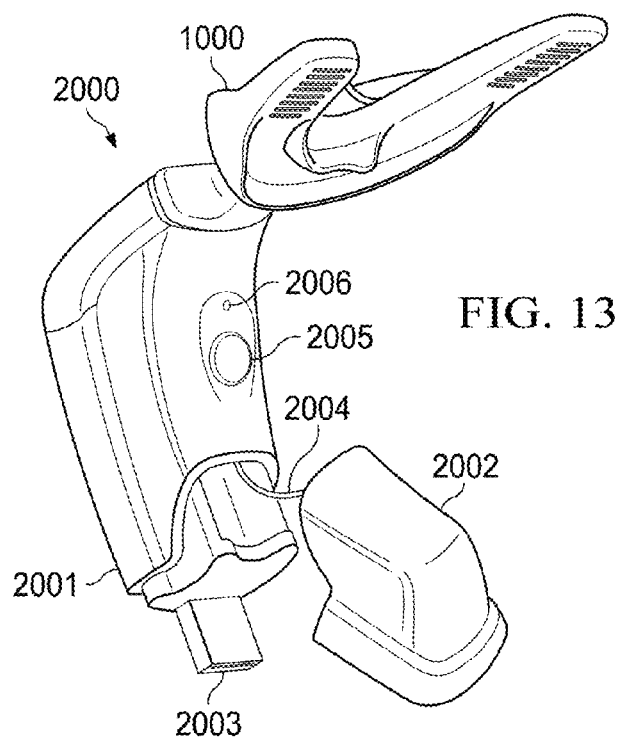
FIG. 13A-B shows a USB embodiment from two angles, wherein the USB is housed inside an access hatch that is tethered to the main body of the housing, and the USB functions for both recharging and data transmission purposes.
Figure 13B:
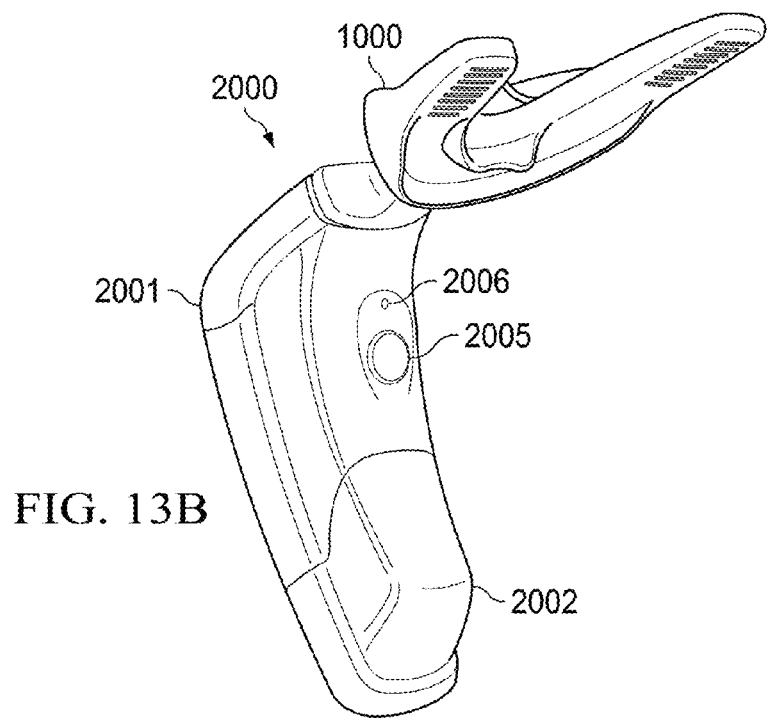

FIG. 13A-B shows the entire device including the bite plate 1000 and extraoral component 2000. The extraoral component comprises a housing 2001, which is ergonomically and aesthetically shaped, and has an on/off switch 2005, such as a membrane button and LED indicator light 2006. Preferably, both the LED and the on/off switch are contained within the same membrane, as this simplifies manufacturing and improves reliability.

Inside the housing is the battery, processor and vibrator, as described herein and not detailed in FIG. 13A-B. Also shown is an access hatch or cap 2002, that is connected to the body of the housing by tether 2004. This prevents the cap from being lost. By "tether" herein, any form of attachment is meant, including a hinge, or coiled line. Inside the hatch, USB connector 2003 is seen, which functions to both transmit data and to allow charging of a rechargeable battery, which is positioned inside the housing and not accessible to the patient.

In preferred embodiments, the access hatch can only be opened with a tool, e.g., via a small recess and cantilevered snap fit catch. This is preferred because it reduces the regulatory burden, avoiding certain IEC 60601 requirements. Also preferred, the battery is not accessible to the patient, necessitating return to the manufacturer when/if the battery needs replacing. This configuration is desirable as further reducing the regulatory burden, reducing the risk of electrostatic discharge (EDS), and also allowing the manufacturer to reset the system and provide any needed refurbishment when/if the battery is changed. Further, the battery is expected to last throughout the treatment period, and replacements should rarely be required.

Figure 14A:
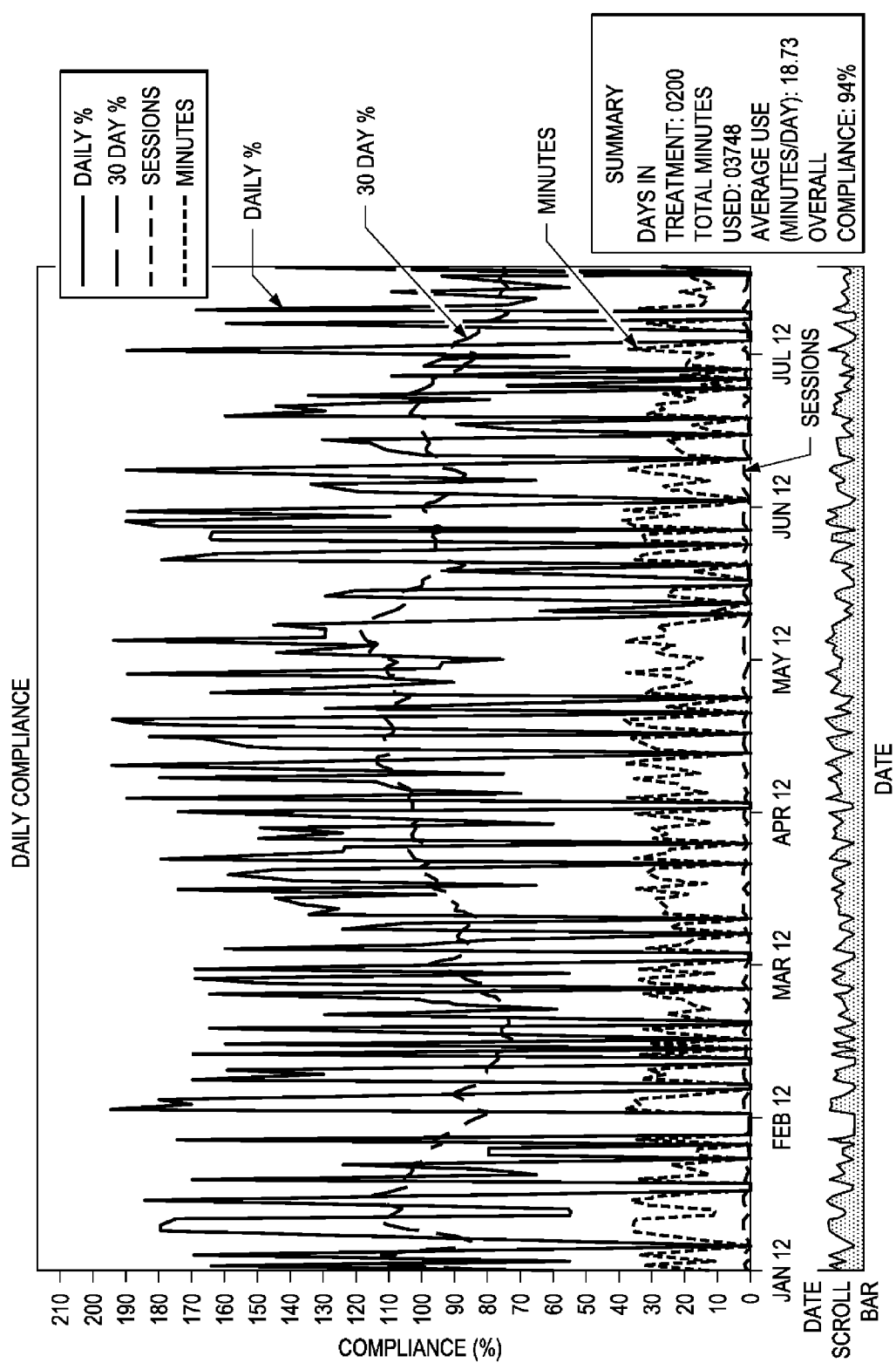
FIG. 14A-B shows exemplary usage data graphics.
Figure 14B:
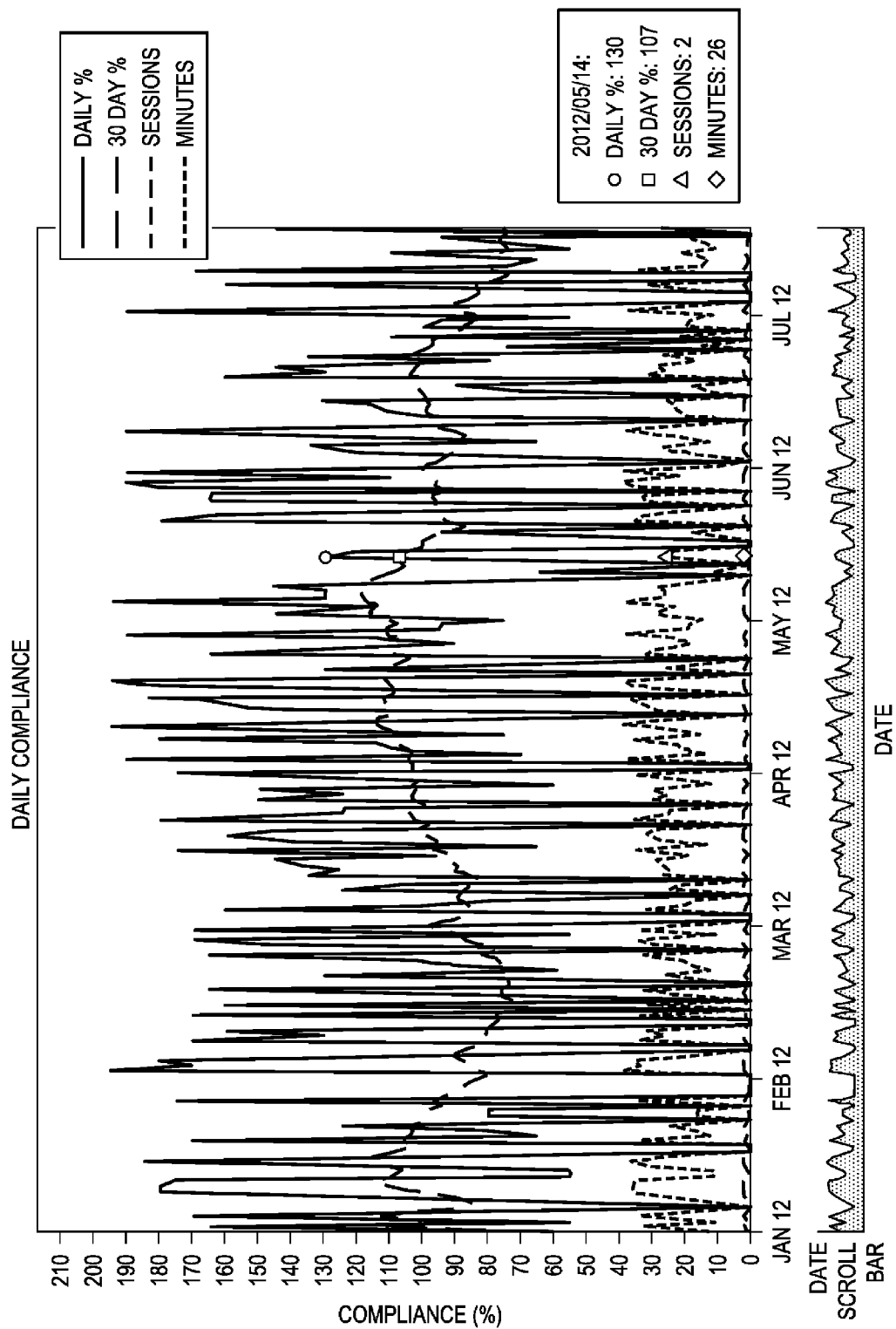

The processor collects raw usage data, including date and length of use. A certain amount of java code is contained in the chip, turning the USB into a virtual flash drive, but any suitable code can be used. Thus, when the device is plugged into a computer, the code converts the raw data into suitable graphics, as shown in FIG. 14A-B. Shown is date on the x axis, and usage (% compliance, minutes of use, and numbers of uses, all on the same scale) on the y axis. The x axis is equipped with scroll bars, which allow the practitioner to review the data more closely if desired (e.g. expand the time scale).

Daily usage is shown (largest scale data), along with 30 day average daily use (top line, excluding daily use), minutes of use (middle line), and number of uses (bottom-most line). Below the graph, lifetime usage data is summarized. In this instance, the patient used the device once or twice a day, skipping some days, and had an overall compliance of 94%.

When the mouse passes over the data, a given day under the mouse is selected (see dots in FIG. 14B) and the data for that day is displayed on the upper right.

These graphics are not available on the device, which lacks a flash drive and thus cannot be misappropriated or overwritten by patients. Instead, the small amount of code embedded in the processor converts the raw data to a usable form when plugged in and activated. This allows the smallest footprint, reduces regulatory burdens, and still provides convenient data analysis in a variety of forms, which can be used by practitioners and in clinical trials. JavaScript code from an open source package was used in our prototypes, called "dygraphs JavaScript Visualization Library" (see code.google.com/p/dygraphs/), but any other code could be used as well.

Setting the time and data on the prototype device requires an external source of communicating to the device. With the device connected to a personal computer the user will navigate to the compliance data report which will display instructions for the user to initiate a file save operation using their browser, which will access the product FLASH drive and enters a file name to save such as "DateTime". The browser will save the compliance report on the product FLASH drive under a given file name. The product will use the file creation date provided by the operating system in the file save operation to set the real time clock in the device.

The cyclic force or vibration applied to the bite plate, tooth positioner, or other intraoral functional appliance is at frequencies between 1 to 1000 Hz (preferably 10-100 Hz and most preferred 20-40 Hz) and a force of 0.01-2 Newtons (or 0.1-0.5 or 0.2 Newtons) for a period of 1-60 minutes, preferably about 1-30 or 1-10 minutes or 20 minutes. This is followed by a period of recovery, ranging from 2-24 hours, preferably from 4-12 hours, and the cycle is repeated until one or more teeth are successfully moved.

More particularly, the orthodontic appliance of the invention has a vibrational source capable of providing a vibratory force at a frequency of between 20 to 40 Hz or 30 Hz and a force of 0.1-0.5 Newtons or 0.25 Newtons. Excess force is generally unpleasant to the patient, especially force coupled with high frequency.

Figure 16:
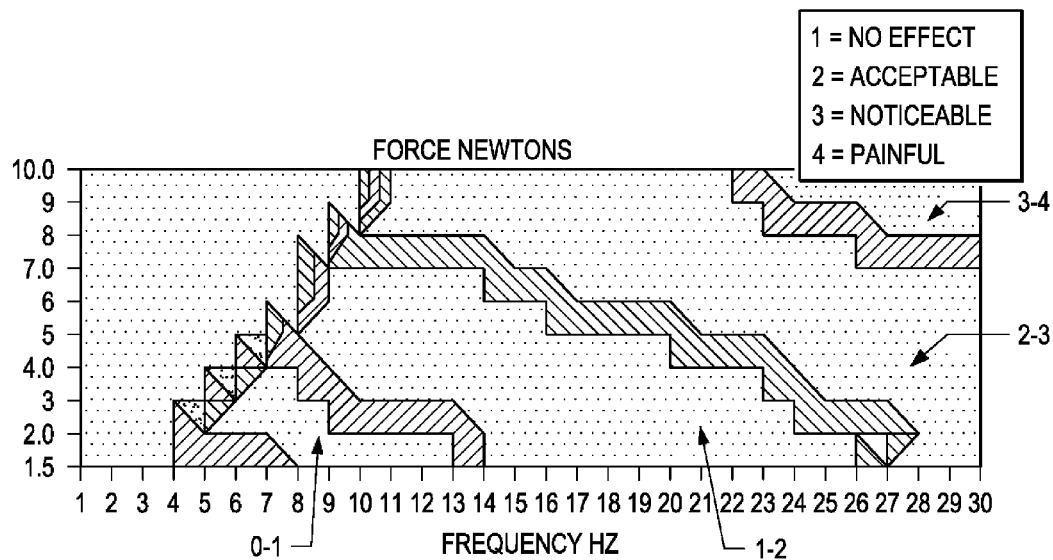
FIG. 16 shows a graph of force in Newtons on the Y axis, versus frequency in Hz on the X axis, and plotted are patient reactions to the various combinations of force and frequency. Generally, the higher the frequency, the less force should be used in order to provide a device that will have good patent acceptance.

This is demonstrated in the graph at FIG. 16, which illustrates how higher frequencies and forces change patient perception of the device. The graph shows that for patient comfort, a 30 Hz frequency should be coupled with a force of less than 1 Newton, although higher forces can be comfortably used at lower frequencies. Fortunately, research has also confirmed that very low magnitude force will suffice to significantly impact the rate of orthodontic remodeling.

While at least one study has shown increased hip density at 1 Hz (walking speed), suggesting that lower frequencies may have efficacy, further work will be required to elucidate the optimal frequencies for orthodontic applications. Furthermore, results applicable to long bone skeletal structure may well differ from optimal frequencies for orthodontic applications due to the differing biology of the dental structures.

In preferred embodiments these parameters are patient adjustable within clinically efficacious ranges. In addition to capturing and storing usage data, the processor can also control the force and frequency parameters, and appropriate controls or user interface can be provided for same.

Preferably, the vibrating component has a more stable vibrator with improved performance characteristics of decreased sound and low variance frequency and force. In particular, the improved vibrator has a noise level less than 55 dB when measured at 6 inches, a frequency at 20-40 Hz, with a variance of only 2 Hz, and a force of 0.1-0.5 Newtons, with a variance of +−0.05 N, or similar.

Consistency of frequency and force is achieved herein via a feedback loop whereby motor speed is monitored and software adjusts the motor as needed. More particularly, the motor contains an integrated encoder that provides multiple high and low signal outputs per motor revolution. The software counts the time between every encoder event (e.g., a rotating disc with markings thereon can be optically sensed) and compares this to the desired target (e.g., 30 Hz). Based on this comparison, the software then adjusts the pulse width modulation that is driving the motor to increase or decrease speed as appropriate to maintain the desired speed. Accurate controlling of speed also controls the force.

Integrated optical encoders may be preferred, as one type of rotary encoder, but the feedback mechanism can be any known technology. Encoders can be separate or integrated, and be optical, magnetic, or capacitive encoders, or be proximity sensors repurposed to encode. A proportional-integral-derivative controller (PID controller) is another option. The PID is a generic control loop feedback mechanism widely used in industrial control systems.

A DC 5V Motor having off-set weight and 8 line integrated encoder is known to provide these characteristics, but many other vibrators can also provide these performance characteristics, and can be easily tested for same. MicroMo Inc., for example has 8 and 16 line encoders integrated with micromotors available at a variety of voltages, and many other suppliers make similar devices. Preferably the battery is of rechargeable Lithium Ion or Polymer chemistry with a minimum capacity of 100 mA-hours.

Custom devices can also be built, but off the shelf components are less expensive. Therefore, preferably, the motor is the Series SE8G DC Motor, by NMB Technologies. Preferably the battery is a 110 mAh Li—PO battery by Fullriver Battery (601522).

Figure 15A:
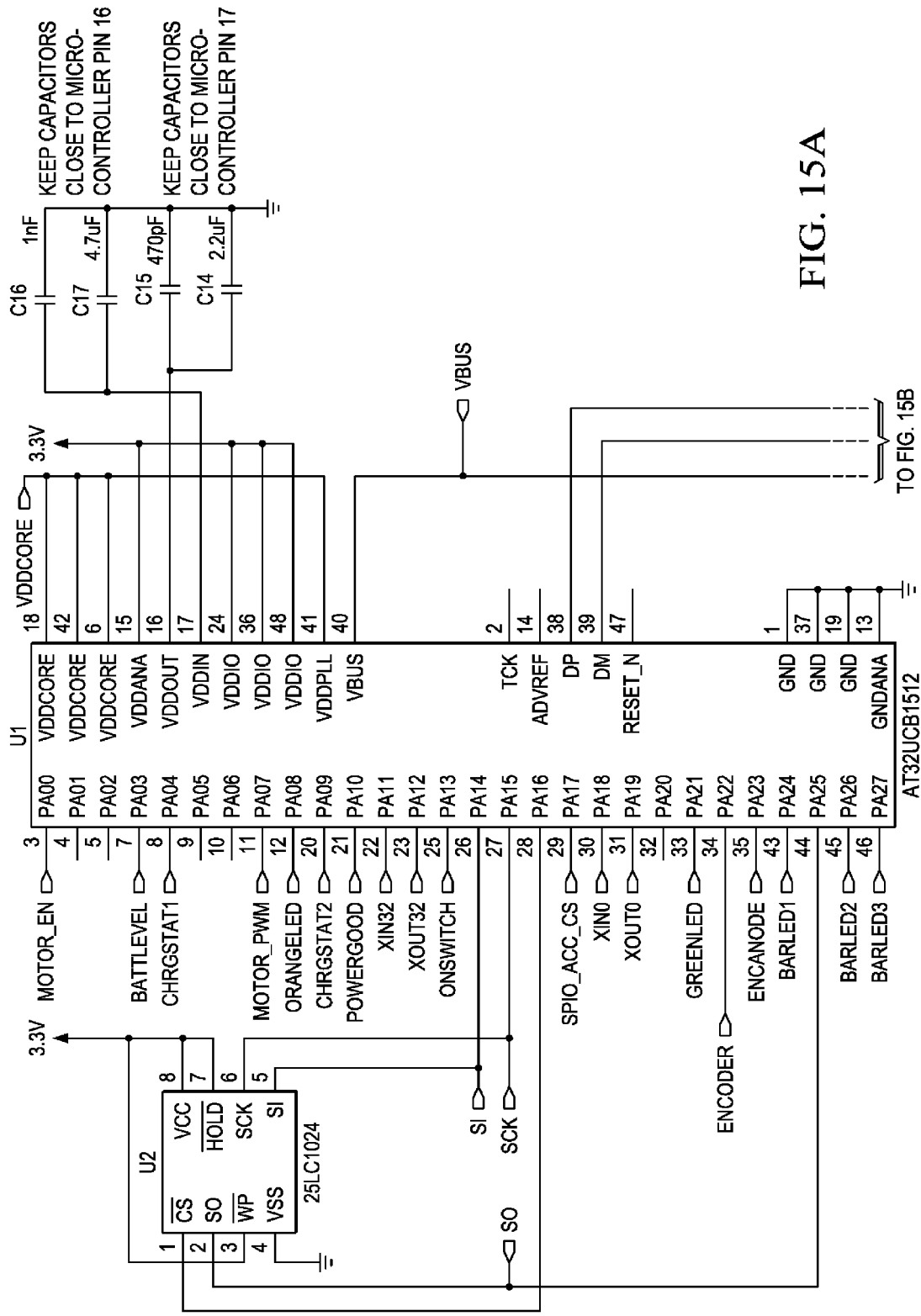
FIGS. 15A-C show an exemplary circuit diagram.
Figure 15B:
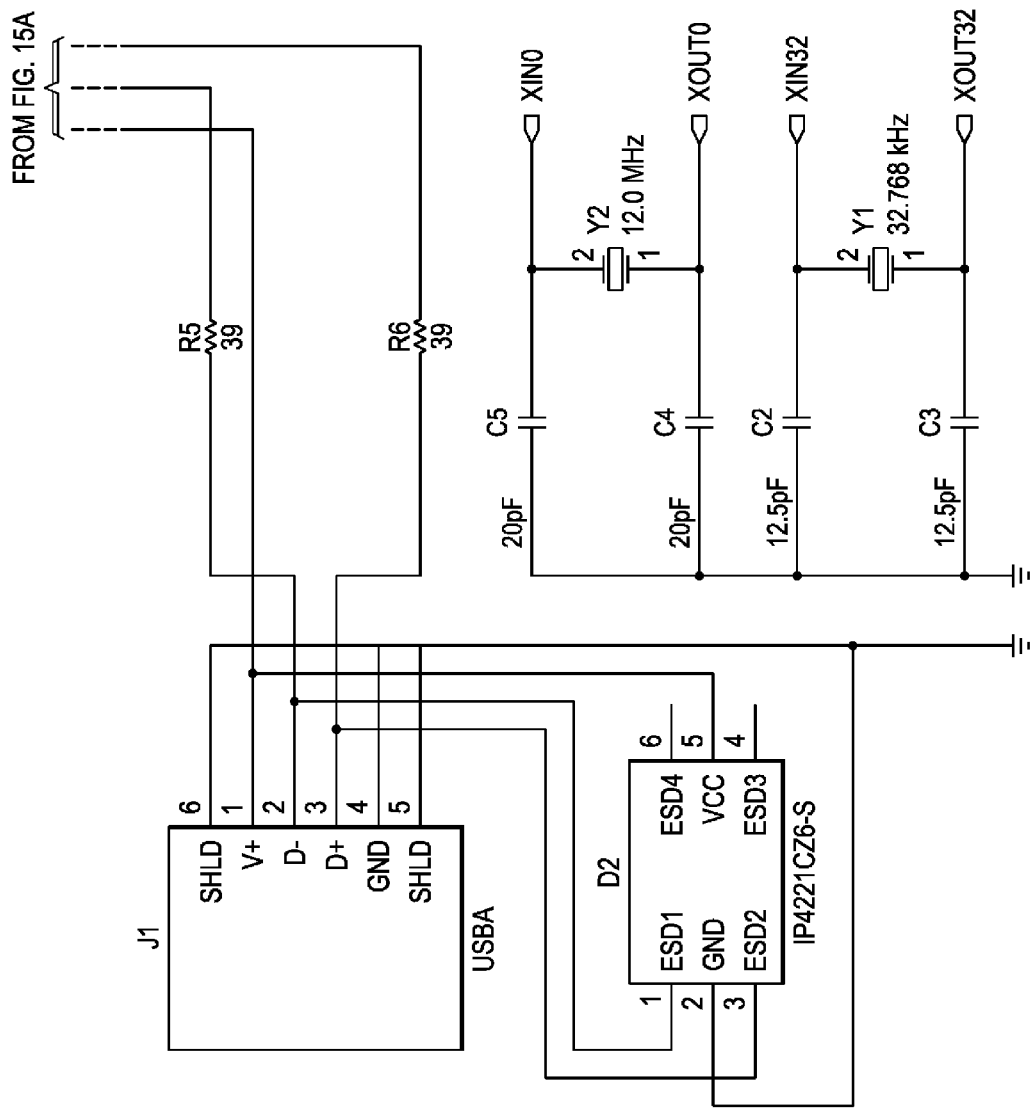
Figure 15C:
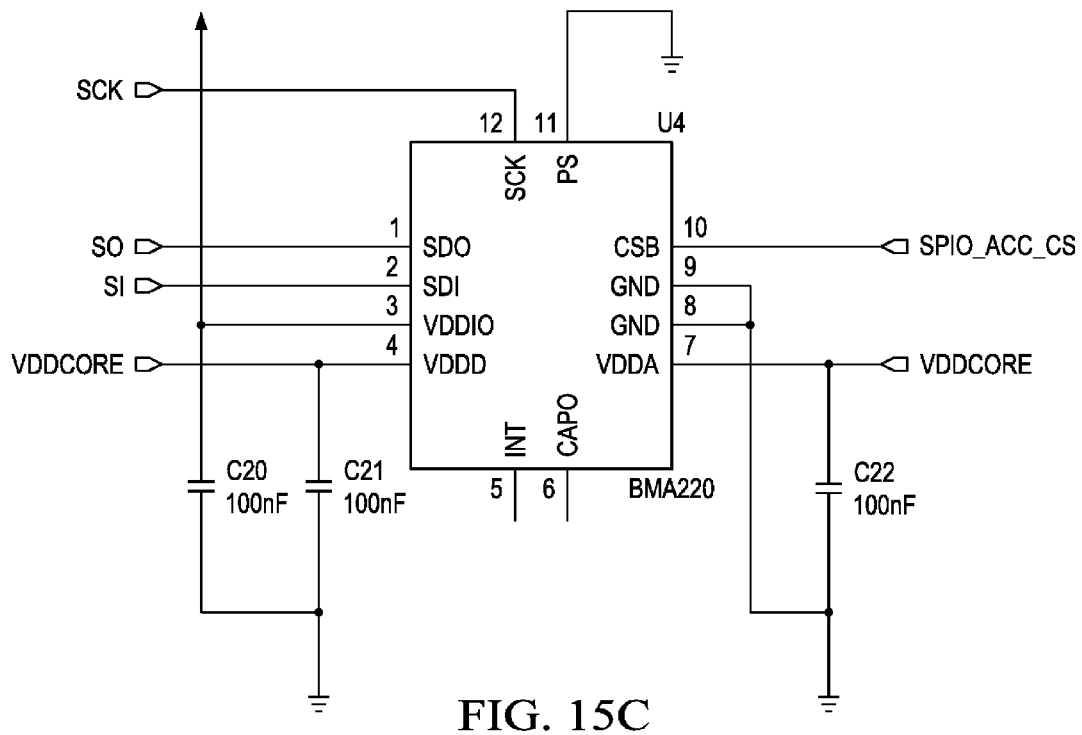

Exemplary circuit diagrams are provided in FIGS. 15A-C. One embodiment thereof is described below.

Processor: The circuit utilizes a 32-bit low power processor to control the vibration motor, USB interface and user interface. The processor interfaces to an EEPROM or external serial flash memory for storage and retrieval of usage data. The processor also interfaces to a digital, triaxial acceleration sensor that is not used currently but may be used in future versions for monitoring device orientation and vibration characteristics for both usage data and safety monitoring.

Power: The power circuit utilizes a battery charge management controller to charge the battery and monitor the battery charge status. Battery voltage is regulated to 3.3 V.

Motor Control: Motor speed is regulated using a low-side transistor switch controlled by the processor via pulse width modulation (Pulse-width modulation or PWM is a modulation technique that controls the width of the pulse, formally the pulse duration, based on modulator signal information, wherein the average value of voltage (and current) fed to the load is controlled by turning the switch between supply and load on and off at a fast pace such that the longer the switch is on compared to the off periods, the higher the power supplied to the load). Motor speed is sensed by the processor by monitoring the digital signal from a reflective optical interrupter that detects transitions on a notched wheel attached to the motor shaft, and then speed adjusted using PWM. To mitigate hazards caused by excessive motor speed, a dedicated voltage regulator limits the motor drive voltage to 1.2 V, thus limiting the maximum motor speed to a safe level. In addition, the processor can disable the voltage regulator if a fault is detected.

User Interface: The user interface circuit drives LED current controlled by the processor. Button press status is monitored by the processor.

A cone beam device (GALILEOS™, by SIRONA™) was utilized to accurately measure both roots and to estimate any resulting root resorption, with imaging in all three planes (sagittal, axial and coronal views). The study was designed to determine if any root resorption greater than 0.5 mm occurred or if there were alterations in root lengths, and no significant losses were found.

The study also measured distances between teeth using a digital caliper. The overall distance in millimeters between the front five teeth, both upper and lower, was calculated during the alignment phase. The gap between teeth due to extractions was measured directly. The overall movement rate during the study was 0.526 mm per week, which is higher than average movement without the device.

We conclude that the device safely increases the rate of orthodontic tooth movement and can be used with either fixed orthodontic appliances or clear aligners, offering flexibility. This is useful given the mix of orthodontic therapies available and particularly since some patients have combination therapy utilizing both fixed orthodontic appliances and clear aligner therapy. Short-term daily use for 20 minutes provides an advantage for patients.

A phase 3 randomized clinical trial was performed with 45 patients, again with 25 grams and 30 Hz. The primary efficacy endpoint for the study was the difference in the weekly rate of tooth movement between the device group and sham-control group.

The results demonstrate that the device described herein can increase the rate of tooth movement when used in conjunction with conventional orthodontics. The results confirm an accelerated tooth movement both during initial alignment (2.06 times or 106% faster) and space closure (1.38 times or 38% faster) phases of orthodontic treatment. Overall treatment time was 50% faster.

Use of the device did not increase the risk of either root resorption or TAD loosening. The only potentially device-related events that occurred in more than one case in this clinical trial related to tooth discomfort, soreness, or numbness, all of which are commonly reported with standard orthodontic treatment. In all cases, the events were mild and transient and none required discontinuation or any significant modification of treatment procedures. Overall satisfaction, as well as eight specific assessments, indicates that patients accepted the treatment well and easily incorporated the use of the device into their daily activities.

The direct clinical benefit from daily use of the device is shortened treatment time. In a case with an extraction space of 6-8 mm, the device will save the patient approximately 11-15 weeks during the space closure phase of orthodontic treatment. However, considering the acceleration of tooth movement during the alignment phase, the reduction to overall treatment time is likely to be even greater. Further improvements in overall compliance will probably also increase the overall acceleration observed.

Figure 17:
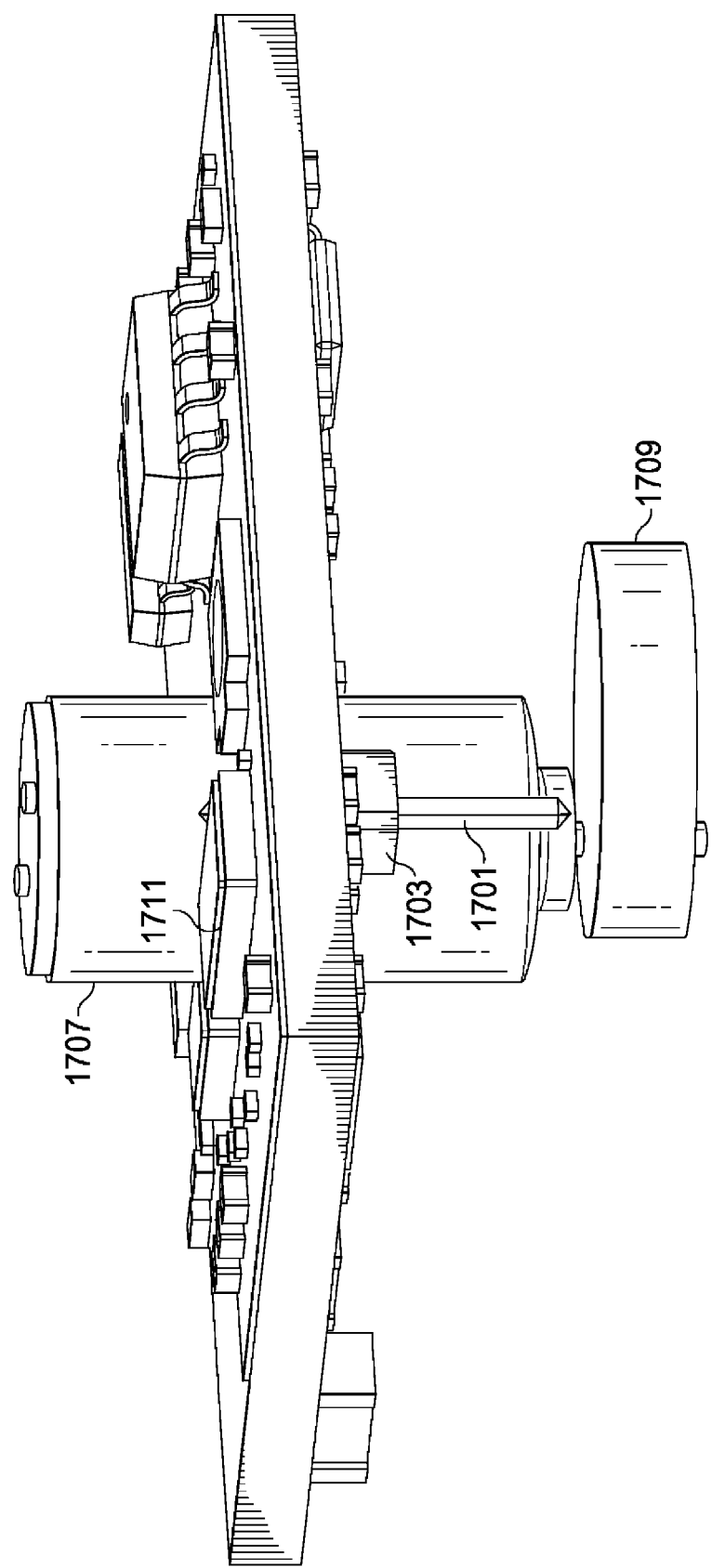
FIG. 17 shows the pins on the circuit board and solid state sensor for sensing motor speed.

FIG. 17 shows the pin headers 1701 and solid state sensor 1703 that allow for electrostatic or capacitive sensing of motor speed. One or more pins of e.g., Arduino pins are attached to the board, and soldered or otherwise operatively connected to a solid state sensor 1703. When a capacitive load (such as the eccentric rotating weight 1709 of motor 1707) is in close proximity to the pins, the sensor detects the change in capacitance as the eccentric rotating mass or ERM 1709 passes close by the pin. By tracking these changes over time, motor speed can be calculated and adjustments made so that motor speed doesn't vary, as required by the specification stated herein. Custom pin heads can be made from nearly any conductive material to take advantage of customized pin shapes to maximize sensing.

The distance-D- the pins should be placed from the ERM can vary from 0.01 mm to 5 mm, depending on the sensitivity of the system and the size of the components. The ability of the sensor to detect the target is determined by the target's size, dielectric constant and distance from the sensor. The larger the target's size, the stronger the capacitive coupling between the probe and the target. Materials with higher dielectric constants are easier to detect than those with lower values. Given the ERM is typically made of metal its dielectric constant is virtually infinite, resulting in excellent sensing capability for a capacitive system. The shorter the distance between target and probe, the stronger the capacitive coupling between the probe and the target.

Ideally, the pins are close, but not so close that they could ever touch, even if the device is jostled or dropped. Distance can vary from 0.05-2 mm, and preferably 0.1-0.5 mm. We have use PCB herein, in combination with 1 pin, the capacitive sensor, and the ERM motor. The processor 1711 used for this was Cypress PSOC42xx CY8C4248LQI-BL483ES, but any custom or off the shelf equivalent could be used. The same processor can be used for all functions on the device, or separate processors could be provided. Herein, we used Cypress PSOC42xx CY8C4248LQI-BL483ES in order to reduce size.

The software needed is fairly straightforward. The time between signal perturbations determines speed, and the software can increase the voltage to the motor to speed it up, or vice versa. The software can be separately provided or be more or less integral with the proximity sensor components. Off the shelf programmable components are available for capacitive sensing, or custom devices can be built, and the dedicated programming can be added thereto.

The Programmable System-on-Chip (PSoC® 4200 Family of mixed-signal programmable embedded system controllers with an ARM® Cortex™-M0 central processing unit ("CPU") may be preferred herein. This device has a 32-bit microcontroller unit ("MCU") Sub-system, has programmable analog and programmable digital capability, low power 1.71-V to 5.5-V operation, allows capacitive sensing, has a segment Liquid Crystal Display ("LCD") drive, serial communication capacity, timing and pulse-width modulation capacity, up to 36 programmable general-purpose input/outputs ("GPIOs"), integrated Bluetooth Low Energy communications, and a PSoC Creator Design Environment that allows fairly easy programming and trouble shooting.

For proximity sensing, the above PsoC chip has the Cypress CapSense Sigma-Delta (CSD), which allegedly provides best-in-class signal to noise ration of >5:1 and water tolerance. A proximity sensor emits an electromagnetic field or a beam of electromagnetic radiation (infrared, for instance), and looks for changes in the field or return signal. The object being sensed is often referred to as the proximity sensor's target. Different proximity sensor targets demand different sensors. For example, a capacitive or photoelectric sensor might be suitable for a plastic target; an inductive proximity sensor always requires a metal target.

The CapSense sensor is supported on all pins in PSoC 4200 through a CapSense Sigma-Delta (CSD) block that can be connected to any pin through an analog mux bus that any GPIO pin can be connected to via an analog switch. CapSense function can thus be provided on any pin or group of pins in a system under software control. A component is provided for the CapSense block to make it easy for the user.

The maximum distance that this sensor can detect is defined "nominal range". Proximity sensors have a high reliability and long functional life because of the absence of mechanical parts and lack of physical contact between sensor and the sensed object.

The GPIO is a generic pin on an integrated circuit whose behavior, including whether it is an input or output pin, can be controlled by the-software at run time.

Another feature that helped us to reduce the size of the device was to use a smaller offset weight in the ERM. Through much research, we have found that an 87% tungsten weight of 1.9 g allows use to reduce size by >50%. Indeed, motor size went from 266 mm$^3$ reduced to 109 mm$^3$ total volume when a 1.9 g 87% tungsten weight was used.

Figure 18A:
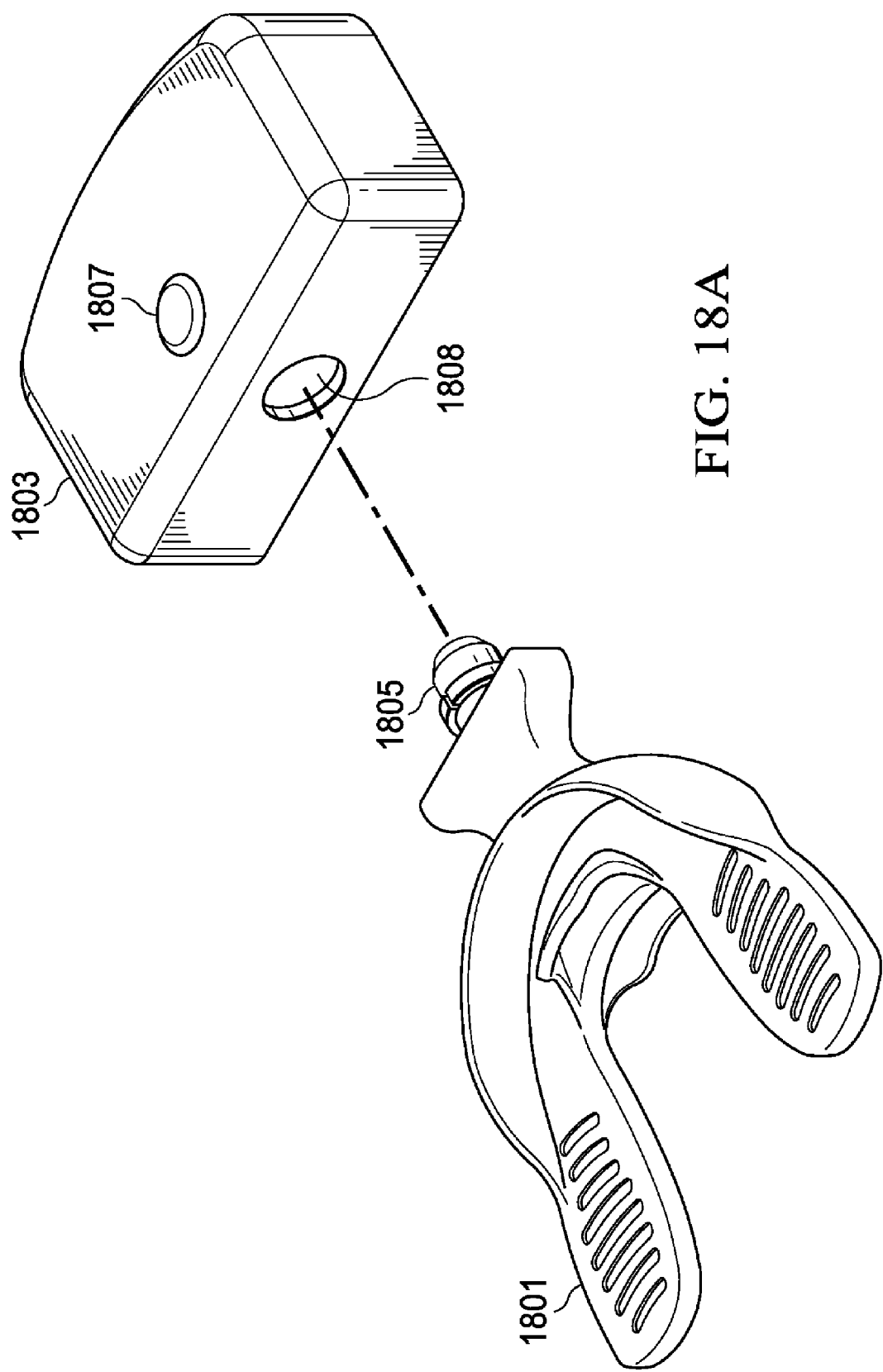
FIG. 18A-B shows a bite plate without inner core, that is molded over the extra-oral activator, and has an access hatch for servicing the electronics.
Figure 18B:
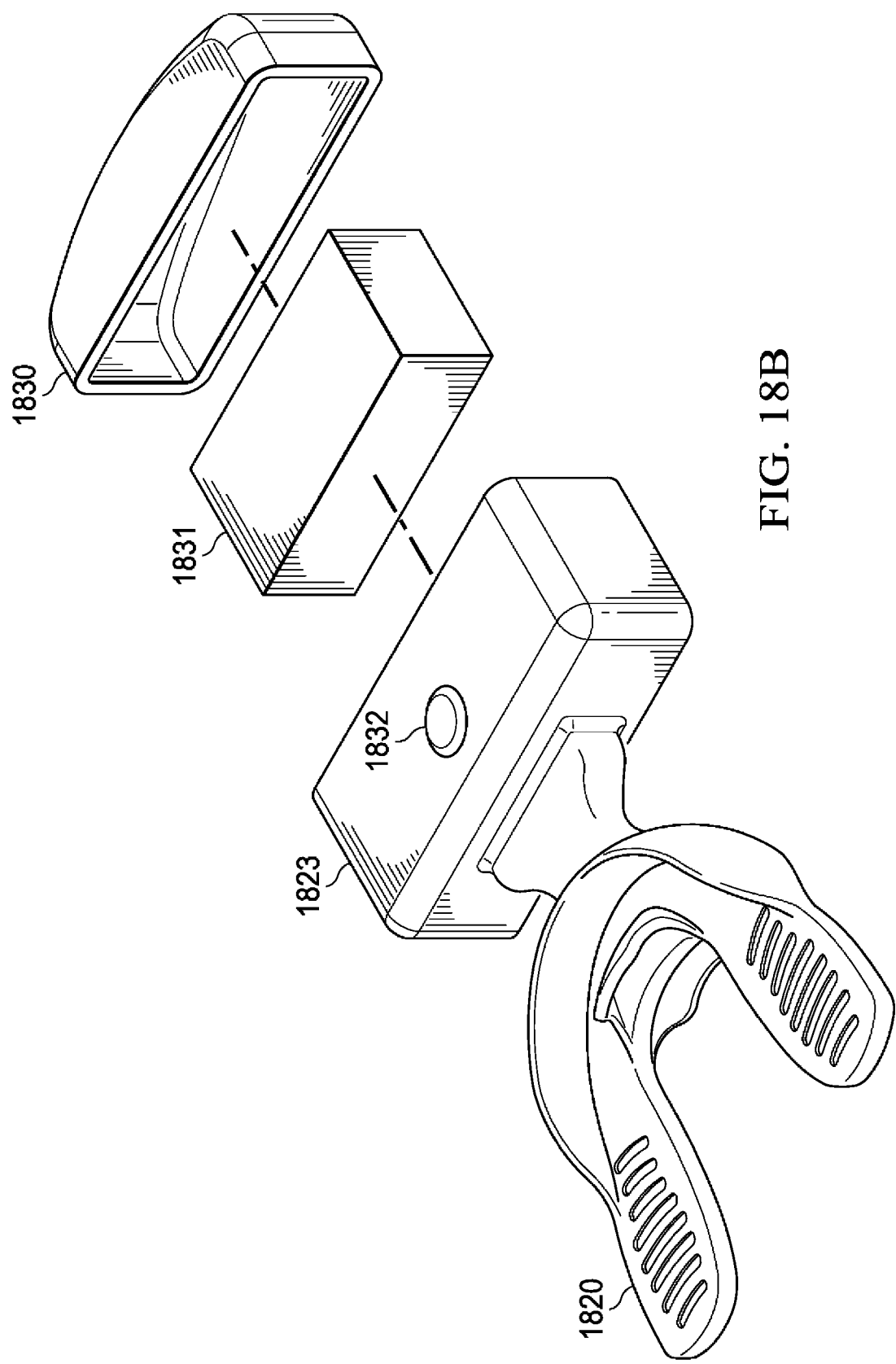

FIGS. 18A and 18B show bite plate embodiments without an inner core, wherein the hardness of material and/or motor weight are increased to compensate for any dampening of vibration by the bite plate. In FIG. 18A, bite plate 1801 has usual vertical ridges or phalanges for contacting vertical surfaces of teeth, and is shaped very similar to the bite plate of FIG. 10. Thus, the various surface and shapes are not discussed herein. The extraoral driver 1803 with activation button 1807 may have a somewhat larger socket 1808 into which the larger stem 1805 fits (or vice versa). Thus, the size of the stem is sufficient for a secure connection, even without the stiff inner core. Alternatively, the stem alone can comprise a stiffer material, or be overmolded over a stiffer material (not shown) for a strong connection. The current configuration has stem 1805 permanently molded directly into the socket 1808 in the manufacturing process so that it is non-detachable.

In FIG. 18B, however, the bite plate 1820 is molded over the driver (not shown) or driver housing 1823, and thus cannot be decoupled therefrom. If desired, an access hatch 1830 allows access to the electronic driver 1831, which can be removed and serviced if needed. Driver 1831 is activated with on/off switch 1832.

FIG. 19 shows yet another bite plate 1901 without inner core, that has cutouts 1903, 1905 at about the canine position, which allow the ends of the bite plate to be brought closer together, or apart, as needed to fit different arch forms. As is well known in the art, the Euro arch (see dotted line 1907) narrows continually from the molars to incisors, whereas the Asian arch (dotted line 1909) is closer to parallel from molars to canines, and has a much more rounded front. Therefore, it is difficult to make a bite plate that fits all patients. However, the large amount of inventory needed for dedicated bite plates is expensive, and takes space to store. This solution allow the same bite plate to fit a broader range of arch forms, though of course child and adult sizes will still be required. Because the material is thermoplastic, a degree of flex can be accommodated, and the molars spread to accommodate the Euro arch, and narrowed to accommodate an Asian arch.

While the invention is described above in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

Each of the following is incorporated by reference in its entirety for all purposes.

60/906,807 filed Mar. 14, 2007, US20080227046, US20080227047, US20100055634, US20120322018, US2013059263, US2013323669, US2011136070, Ser. No. 14/468,100 filed Aug. 25, 2014, and 61/901,154, filed Nov. 7, 2013.

Kau, C. H. "A novel device in orthodontics." Aesthetic Dentistry Today 3:6 (2009): 42-43.

Kau, C. H. "A radiographic analysis of tooth morphology following the use of a novel cyclical force device in orthodontics." Head & Face Medicine 7:14 (2011).

Kau, C. H., How et al., The clinical evaluation of a novel cyclical force generating device [AcceleDent®] in orthodontics, Orthodontic Practice 1(1): 10-15 (2010).

Kopher R A and Mao J J. Suture growth modulated by the oscillatory component of micromechanical strain. 2003. J. Bone and Min Res. 18 (3). pp. 521-528.

Krishtab et al., [Use of vibratory action on the teeth to accelerate orthodontic treatment] [Article in Russian] Stomatologiia (Mosk). 1986 May-June; 65(3):61-3.

Nishimura et. al. Periodontal tissue activation by vibration: Intermittent stimulation by resonance vibration accelerates experimental tooth movement in rats. 2008. Am J Orthod Dentofacial Orthop 133(4) pp. 572-583.

Peptan A I, et. al. Responses of intramembranous bone and sutures upon in-vivo cyclic tensile and compressive loading. 2008. Bone (42) pp. 432-438.

Vij K. and Mao, J J. Geometry and cell density of rat craniofacial sutures during early postnatal development and upon in-vivo cyclic loading. 2006. Bone (38) pp. 722-730.

Werner, Alison. "Acceleration by Vibration." Orthodontic Products (2011): 31, 35.

The invention claimed is:

1. An orthodontic remodeling device, comprising:
   a) an extraoral vibratory source comprising:
      i) an actuator, where said actuator is an offset weight motor;
      ii) a processor that controls said actuator and captures and transmits device usage data;
      iii) a power source that drives said actuator;
   b) an intraoral attachment consisting essentially of a bite plate allowing for contact with occlusal surfaces and allowing contact with upper and lower buccal surfaces of a patient's teeth, wherein said patient biting on said bite plate holds said orthodontic remodeling device in place during use;
   c) said vibratory source being coupled to the intraoral attachment;
   d) wherein said orthodontic remodeling device vibrates at a single frequency selected to be between 0.1 Hz and 400 Hz, and wherein when used together with braces or aligners for 20 minutes daily said device accelerates tooth movement as compared to a patient not using said device;
   wherein a speed of said offset weight motor is controlled with a capacitive sensor comprising one or more header pins having a weak electrostatic (ES) field that is disrupted when said offset weight passes by, said header pins operably coupled to a solid state ES field sensor operably coupled to the processor, wherein said processor detects said speed by detecting said disrupted ES field, and controls said speed such that said speed varies by less than 2 Hz.

2. The device of claim 1, wherein said offset weight on said offset weight motor is at least 87% tungsten.

3. The device of claim 1, wherein said bite plate is made of a single thermoplastic material.

4. The device of claim 3, wherein said bite plate has a pair of cutouts on a lingual side thereof at a position near canine teeth of a patient, such that molar ends of said bite plate can be flexed at least 1 cm closer together or 1 cm farther apart.

5. The device of claim 4, wherein said bite plate is 2 mm or less in thickness at occlusal surfaces thereof.

6. The device of claim 4, wherein said bite plate is 1.5 mm or less in thickness at occlusal surfaces thereof.

7. The device of claim 3, wherein said single thermoplastic material forms said bite plate and completely covers said extraoral vibratory source.

8. The device of claim 7, wherein an access hatch is provided in said single thermoplastic material such that said extraoral vibratory source can be accessed.

9. The device of claim 7, which is waterproof.

10. The device of claim 7, which is water resistant.

11. The device of claim 1, wherein said device vibrates at a single frequency between 20-40 Hz and at a single force between 0.1-0.5 Newtons.

12. The device of claim 1, wherein said device vibrates at 30 Hz and 0.2 Newtons.

13. The device of claim 1, wherein said device vibrates at a single frequency between 20-40 Hz with a variance of ±2 Hz and a single force between 0.1-0.5 N with a variance of ±0.05 N.

14. The device of claim 1, wherein said device vibrates at 30 Hz with a variance of ±2 Hz and at 0.2 N with a variance of ±0.05 N.

15. A faster method of orthodontic remodeling, comprising: a) a patient wearing braces or aligners using the device of claim 13 and biting said bite plate, and b) activating said device for about 20 minutes daily, wherein said method provides 50% faster tooth movement as compared to without using said device.

16. A faster method of orthodontic remodeling, comprising: a) a patient wearing braces or aligners using the device of claim 14 and biting said bite plate, and b) activating said device for about 20 minutes daily, wherein said method provides 50% faster tooth movement as compared to without using said device.

17. An orthodontic remodeling device, comprising:
   a) an extraoral vibratory source comprising:
      i) an actuator comprising an offset weight motor;
      ii) a processor that controls said actuator;
      iii) a power source that drives said actuator;
   b) an intraoral attachment consisting essentially of a bite plate allowing for contact with occlusal surfaces and allowing contact with upper and lower buccal surfaces of a patient's teeth, wherein said patient biting on said bite plate holds said orthodontic remodeling device in place during use;
   c) said vibratory source being coupled to the intraoral attachment;
   d) wherein said orthodontic remodeling device vibrates at a single frequency selected to be between 0.1 Hz and 400 Hz;
   e) wherein a speed of said offset weight motor is controlled with a capacitive sensor comprising one or more header pins having a weak electrostatic (ES) field that is disrupted when said offset weight passes by, said header pins operably coupled to a solid state ES field sensor operably is coupled to said processor, wherein said processor detects said speed by detecting said disrupted ES field, and controls said speed such that said speed varies by less than 2 Hz; and
   f) wherein when used together with braces or aligners for 20 minutes daily said device accelerates tooth movement as compared to a patient not using said device.

* * * * *